(12) United States Patent
Nirogi et al.

(10) Patent No.: US 10,973,831 B2
(45) Date of Patent: Apr. 13, 2021

(54) FLUOROPIPERIDINE COMPOUNDS AS PURE 5-HT 6 RECEPTOR ANTAGONISTS

(71) Applicant: SUVEN LIFE SCIENCES LIMITED, Hyderabad-Telangana (IN)

(72) Inventors: Ramakrishna Nirogi, Hyderabad (IN); Anil Karbhari Shinde, Hyderabad (IN); Abdul Rasheed Mohammed, Hyderabad (IN); Rajesh Kumar Badange, Hyderabad (IN); Kumar Bojja, Hyderabad (IN); Vinod Kumar Goyal, Hyderabad (IN); Santosh Kumar Pandey, Hyderabad (IN); Jagadeesh Babu Thentu, Hyderabad (IN); Venkateswarlu Jasti, Hyderabad (IN)

(73) Assignee: SUVEN LIFE SCIENCES LIMITED, Hyderabad (IN)

( * ) Notice: Subject to any disclaimer, the term of this patent is extended or adjusted under 35 U.S.C. 154(b) by 0 days.

(21) Appl. No.: 16/635,893

(22) PCT Filed: Aug. 6, 2018

(86) PCT No.: PCT/IB2018/055894
§ 371 (c)(1),
(2) Date: Jan. 31, 2020

(87) PCT Pub. No.: WO2019/030641
PCT Pub. Date: Feb. 14, 2019

(65) Prior Publication Data
US 2020/0155560 A1    May 21, 2020

(30) Foreign Application Priority Data

Aug. 7, 2017    (IN) .............................. 201741028024

(51) Int. Cl.

| | |
|---|---|
| *A61K 31/538* | (2006.01) |
| *A61P 25/28* | (2006.01) |
| *C07D 413/04* | (2006.01) |
| *C07D 413/14* | (2006.01) |
| *A61K 31/13* | (2006.01) |
| *A61K 31/24* | (2006.01) |
| *A61K 31/445* | (2006.01) |
| *A61K 31/473* | (2006.01) |
| *A61K 31/155* | (2006.01) |

(52) U.S. Cl.
CPC ............ *A61K 31/538* (2013.01); *A61K 31/13* (2013.01); *A61K 31/155* (2013.01); *A61K 31/24* (2013.01); *A61K 31/445* (2013.01); *A61K 31/473* (2013.01); *A61P 25/28* (2018.01); *C07D 413/04* (2013.01)

(58) Field of Classification Search
CPC ..... A61K 31/538; A61P 25/28; C07D 413/04; C07D 413/14
See application file for complete search history.

(56) References Cited

U.S. PATENT DOCUMENTS 7,378,415 B2    5/2008 Sethofer et al.

OTHER PUBLICATIONS

European Patent Office, Written Opinion of the International Searching Authority, PCT/IB2018/055894, Oct. 31, 2018, Munich, Germany.
European Patent Office, International Search Report, PCT/IB2018/055894, dated Oct. 31, 2018, Rijswijk, Netherlands.
European Patent Office, Written Opinion of the International Searching Authority, PCT/IB2018/055894, dated Oct. 31, 2018, Munich, Germany.
Perry E.K. (1994) Cholinergic Component of Cognitive Impairment in Dementia. In: Burns A., Levy R. (eds) Dementia.

*Primary Examiner* — Brenda L Coleman
(74) *Attorney, Agent, or Firm* — IpHorgan Ltd.

(57) ABSTRACT

The present invention relates to fluoropiperidine compounds of formula (I), their stereoisomers, isotopic forms or pharmaceutically acceptable salts thereof as 5-HT6 receptor antagonists. In particular the present invention discloses the methods of preparation, pharmaceutical composition, combinations and use of fluoropiperidine compounds, their stereoisomers, isotopic forms or pharmaceutically acceptable salts thereof.

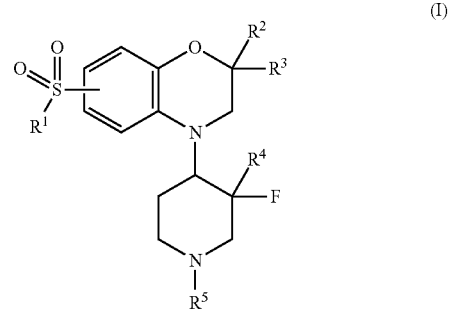

11 Claims, 2 Drawing Sheets

(a)

(b)

(a) Data expressed as Mean ± S.E.M. *$p<0.05$, *$p<0.001$ Vs donepezil alone (Bonferroni's posttest). (b) Cumulative increases in neurotransmitter above baseline expressed as a percentage of the area under the curve ± S.E.M. $p<0.01$ Vs donepezil alone (Unpaired t Test)

(a)

(b)

(a) Data expressed as Mean ± S.E.M. $p<0.01$, *$p<0.001$ Vs donepezil and memantine (Bonferroni's post test). (b) Cumulative increases in neurotransmitter above baseline expressed as a percentage of the area under the curve ± S.E.M. **$p<0.01$ Vs donepezil and memantine (Unpaired t Test).

FLUOROPIPERIDINE COMPOUNDS AS PURE 5-HT 6 RECEPTOR ANTAGONISTS

CROSS REFERENCE TO RELATED APPLICATIONS

This application is a national stage completion application of PCT Application No. PCT/IB2018/055894, filed Aug. 6, 2018, and claims priority from India Application No. 201741028024, filed Aug. 7, 2017. Each of these applications is incorporated by reference herein in its entirety.

FIELD OF THE INVENTION

The present invention relates to fluoropiperidine compounds, their stereoisomers, isotopic forms or pharmaceutically acceptable salts thereof as 5-Hydroxytryptamine 6 receptor (5-HT$_6$R) antagonists. In particular the present invention discloses the methods of preparation, pharmaceutical composition, combinations and use of fluoropiperidine compounds, their stereoisomers, isotopic forms or pharmaceutically acceptable salts thereof.

BACKGROUND OF INVENTION

The disturbance in the neurotransmitter, 5-hydroxytryptamine (5-HT) or serotonin was implicated in various central nervous system disorders such as anxiety, depression, neurodegenerative disorders, cognitive disorders or motor incoordination disorders. Serotonin is localized in the central and peripheral nervous systems (CNS & PNS) and is known to play a vital role in many biological processes. The up regulation or de-regulation of it is involved in conditions including cognitive disorders, psychiatric disorders, motor incoordination, feeding behavioral disorders, sexual disorders, neuroendocrine regulation disorders and among others. The 5-HT receptor subtypes include 5-HT$_1$, 5-HT$_2$, 5-HT$_3$, 5-HT$_4$, 5-HT$_5$, 5-HT$_6$, 5-HT$_7$ and the isoforms such as 5-HT$_{2A}$, 5-HT$_{2B}$, 5-HT$_{2C}$, 5-HT$_{4A}$, 5-HT$_{4B}$, 5-HT$_{4D}$ and 5-HT$_{4E}$.

The 5-Hydroxytryptamine 6 receptor (5-HT$_6$R) subtype was first identified in 1993 and is a member of GPCR family. The 5-HT$_6$R is almost exclusively expressed in the brain, particularly in hippocampus and frontal cortex which are associated with cognition (*Molecular Pharmacology*, 1993, 43, 320-327). Activation of 5-HT$_6$R usually represses cholinergic function (*British Journal of Pharmacology*, 1999, 126, 1537-1542), whereas blockade of the receptor improves the cognitive functions.

Recent studies have shown that antagonism of this receptor by several investigational compounds improved learning and memory in animal models (*CNS & Neurological Disorders—Drug Targets*, 2004, 3, 59-79). Therefore, the antagonism of the 5-HT$_6$ receptor can potentially provide an effective treatment for different cognitive disorders.

The U.S. Pat. No. 7,378,415 patent disclosed the benzoxazine and quinoxaline compounds, as shown below, having 5-HT$_6$ and 5-HT$_{2A}$ receptor affinity for the treatment of certain CNS disorders.

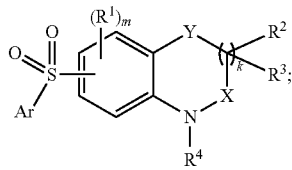

The clinical candidates, Idalopirdine (Lu AE58054) and Cerlapirdine (SAM-531), which are 5-HT$_6$R antagonists and also showed affinity towards 5-HT$_{2A}$ receptors, are discontinued from the clinical trials.

Therefore, the aim of the present invention is to provide the compounds having potent 5-HT$_6$ receptor affinity with minimal or no affinity towards 5-HT$_{2A}$ receptor and also to provide the compounds having good safety profile. The instant invention provides the fluoropiperidine compounds that are highly selective towards 5-HT$_6$ receptor with minimal or no affinity towards 5-HT$_{2A}$ receptor. A person ordinary skilled in the art would not have thought that the introduction of specific group (fluoro) at a specific position of the fluoropiperidine derivatives will result in improvement of selectivity over 5-HT$_{2A}$ receptor and possess better safety profile. These observations were highly surprising and unexpected.

SUMMARY OF THE INVENTION

In first aspect, the present invention relates to fluoropiperidine compound of formula (I),

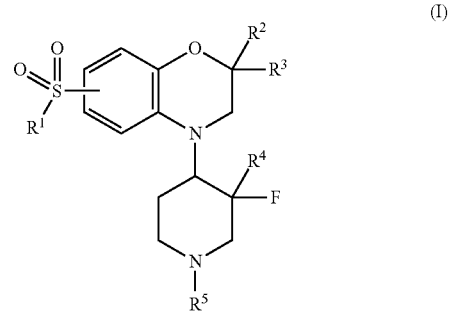

wherein:
R$^1$ represents phenyl or pyridyl; wherein the phenyl or pyridyl is optionally substituted with one or more groups selected from halogen, (C$_{1-6}$)-alkyl or halo(C$_{1-6}$)-alkyl;
R$^2$ represents hydrogen or (C$_{1-6}$)-alkyl;
R$^3$ represents hydrogen or (C$_{1-6}$)-alkyl; or R$^2$ and R$^3$ can combine together to form (C$_{3-6}$)-cycloalkyl;
R$^4$ represents hydrogen, (C$_{1-6}$)-alkyl or halo(C$_{1-6}$)-alkyl;
R$^5$ represents hydrogen, (C$_{1-6}$)-alkyl, halo(C$_{1-6}$)-alkyl or —(CH$_2$)$_{0-3}$—(C$_{3-6}$)-cycloalkyl;
or a stereoisomer or an isotopic form or a pharmaceutically acceptable salt thereof.

In another aspect, the present invention relates to the processes for preparing the compound of formula (I), or a stereoisomer or an isotopic form, or a pharmaceutically acceptable salt thereof.

In yet another aspect, the present invention relates to pharmaceutical composition containing a therapeutically effective amount of at least one compound of formula (I), or a stereoisomer or an isotopic form, or a pharmaceutically acceptable salt thereof and pharmaceutically acceptable excipients or carriers.

In yet another aspect, the present invention relates to the combination of compound of formula (I) or a pharmaceutical salt thereof, an acetylcholinesterase inhibitor and a NMDA receptor antagonist, for use in the treatment of cognitive disorders.

In yet another aspect, the present invention relates to the combination of compound of formula (I) or a pharmaceutical salt thereof and an acetylcholinesterase inhibitor, for use in the treatment of cognitive disorders.

In yet another aspect, the present invention relates to the combination of compound of formula (I) or a pharmaceutical salt thereof and a NMDA receptor antagonist, for use in the treatment of cognitive disorders.

In yet another aspect, the present invention relates to compound of formula (I), or a stereoisomer or an isotopic form or a pharmaceutically acceptable salt thereof, for use as 5-$HT_6$ receptor antagonist.

In yet another aspect, the present invention relates to compound of formula (I), or a stereoisomer or an isotopic form or a pharmaceutically acceptable salt thereof, for use in the treatment of cognitive disorders.

In another aspect, the present invention relates to a method for the treatment of cognitive disorders, comprising administering to a patient in need thereof, a therapeutically effective amount of a compound of formula (I), or a stereoisomer or an isotopic form or a pharmaceutically acceptable salt thereof.

In yet another aspect, the present invention relates to use of the compound of formula (I), or a stereoisomer, or an isotopic form or a pharmaceutically acceptable salt thereof, for the manufacture of a medicament for the treatment of cognitive disorders.

BRIEF DESCRIPTION OF THE DIAGRAMS

DETAILED DESCRIPTION OF THE INVENTION

Figure 1:
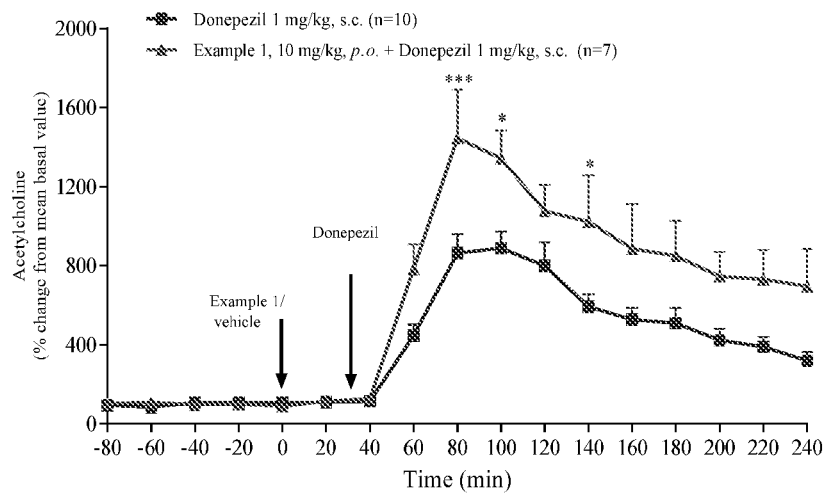
FIG. 1 depicts the effect of example 1 and donepezil combination on extracellular levels of acetylcholine in ventral hippocampus of male Wistar rats.
Figure 1:
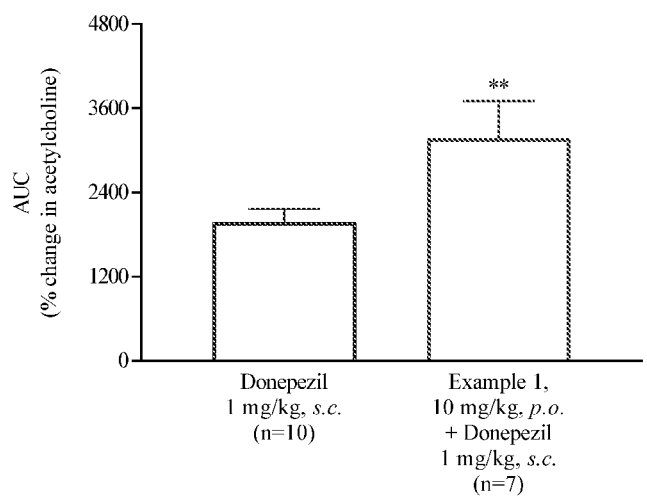

Unless otherwise stated, the following terms used in the specification and claims have the meanings given below:

The term, "($C_{1-6}$)-alkyl" as used herein refers to branched or straight chain aliphatic hydrocarbon containing 1 to 6 carbon atoms. Examples of ($C_{1-6}$)-alkyl include methyl, ethyl, n-propyl, isopropyl, n-butyl, isobutyl, sec-butyl, tert-butyl, pentyl and hexyl.

The term, "halogen" or "halo" as used herein refers to fluorine, chlorine, bromine or iodine. Preferably, halogen is fluorine, chlorine or bromine. More preferably halogen is fluorine.

The term "halo($C_{1-6}$)-alkyl" as used herein refers to ($C_{1-6}$)-alkyl as defined above wherein one or more hydrogens of the same or different carbon atom is substituted with same or different halogens. Examples of halo($C_{1-6}$)-alkyl include fluoromethyl, chloromethyl, fluoroethyl, difluoromethyl, dichloromethyl, trifluoromethyl, difluoroethyl, chlorofluoroethyl and the like.

The term, "($C_{3-6}$)-cycloalkyl" as used herein refers to saturated monocyclic hydrocarbon ring containing three to six carbon atoms. Examples of ($C_{3-6}$)-cycloalkyl group include cyclopropyl, cyclobutyl, cyclopentyl, and cyclohexyl.

The phrase, "therapeutically effective amount" is defined as an amount of a compound of the present invention that (i) treats the particular disease, condition or disorder (ii) eliminates one or more symptoms of the particular disease, condition or disorder (iii) attenuates the symptoms of the particular disease, condition or disorder (iv) delays the onset of one or more symptoms of the particular disease, condition or disorder described herein.

The term, "isotopic form" as used herein refers to the compound of formula (I) wherein one or more atoms of compound of formula (I) are substituted by their respective isotopes. For example, isotopes of hydrogen include $^2$H (deuterium) and $^3$H (tritium).

The term, "stereoisomers" as used herein refers to isomers of compound of formula (I) that differ in the arrangement of their atoms in space. Compounds disclosed herein may exist as single stereoisomer, racemate and/or mixtures of enantiomers and/or diastereomers. All such single stereoisomer, racemates and mixtures thereof are intended to be within the scope of the present invention.

The term, "pharmaceutically acceptable salt" as used herein refers to salts of the active compound i.e. the compound of formula (I), and are prepared by reaction with the appropriate acid or acid derivative, depending on the particular substituents found on the compounds described herein.

The term, "cognitive disorder" as used herein refers to a group of mental health disorders that principally affect learning, memory, perception, problem solving, and include amnesia, dementia, and delirium. Cognitive disorders can be idiopathic or result due to disease, disorder, ailment or toxicity. Preferably the cognitive disorder mentioned here is dementia. Examples of dementia includes but not limited to, dementia in Alzheimer's disease, dementia in Parkinson's disease, dementia in Huntington's disease, dementia associated with Down syndrome, dementia associated with Tourette's syndrome, dementia associated with post menopause, frontotemporal dementia, Lewy body dementia, Vascular dementia, dementia in HIV, dementia in Creutzfeldt-Jakob disease, substance-induced persisting dementia, dementia in Pick's disease, dementia in schizophrenia, dementia in general medical conditions and senile dementia.

EMBODIMENTS

The present invention encompasses all the compounds described by the compound of formula (I) without any limitation, however, preferred aspects and elements of the invention are discussed herein in the form of the following embodiments.

In second aspect, the present invention relates to the compound of formula (I)

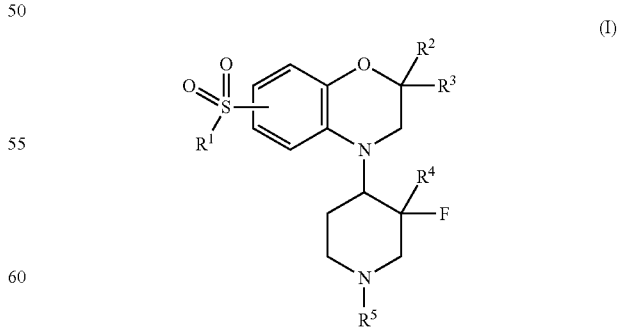

wherein:
$R^1$ represents phenyl or pyridyl; wherein the phenyl or pyridyl is optionally substituted with one or more groups selected from halogen, ($C_{1-6}$)-alkyl or halo($C_{1-6}$)-alkyl;

$R^2$ represents hydrogen or $(C_{1-6})$-alkyl;

$R^3$ represents hydrogen or $(C_{1-6})$-alkyl; or $R^2$ and $R^3$ can combine together to form $(C_{3-6})$-cycloalkyl;

$R^4$ represents hydrogen, $(C_{1-6})$-alkyl or halo$(C_{1-6})$-alkyl;

$R^5$ represents hydrogen, $(C_{1-6})$-alkyl, halo$(C_{1-6})$-alkyl or —$(CH_2)_{0-3}$—$(C_{3-6})$-cycloalkyl;

or a stereoisomer or an isotopic form or a pharmaceutically acceptable salt thereof.

In another aspect, the present invention relates to the compound of formula (Ia), derived from the compound of formula (I),

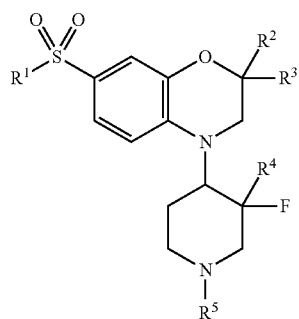

(Ia)

wherein:
$R^1$ represents phenyl or pyridyl; wherein the phenyl or pyridyl is optionally substituted with one or more groups selected from halogen, $(C_{1-6})$-alkyl or halo$(C_{1-6})$-alkyl;

$R^2$ represents hydrogen or $(C_{1-6})$-alkyl;

$R^3$ represents hydrogen or $(C_{1-6})$-alkyl; or $R^2$ and $R^3$ can combine together to form $(C_{3-6})$-cycloalkyl;

$R^4$ represents hydrogen, $(C_{1-6})$-alkyl or halo$(C_{1-6})$-alkyl;

$R^5$ represents hydrogen, $(C_{1-6})$-alkyl, halo$(C_{1-6})$-alkyl or —$(CH_2)_{0-3}$—$(C_{3-6})$cycloalkyl;

or a stereoisomer, or an isotopic form or a pharmaceutically acceptable salt thereof.

In another aspect, the present invention relates to the compound of formula (Ib), derived from the compound of formula (I),

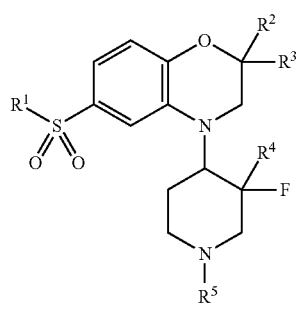

(Ib)

wherein:
$R^1$ represents phenyl or pyridyl; wherein the phenyl or pyridyl is optionally substituted with one or more groups selected from halogen, $(C_{1-6})$-alkyl or halo$(C_{1-6})$-alkyl;

$R^2$ represents hydrogen or $(C_{1-6})$-alkyl;

$R^3$ represents hydrogen or $(C_{1-6})$-alkyl; or $R^2$ and $R^3$ can combine together to form $(C_{3-6})$-cycloalkyl;

$R^4$ represents hydrogen, $(C_{1-6})$-alkyl or halo$(C_{1-6})$-alkyl;

$R^5$ represents hydrogen, $(C_{1-6})$-alkyl, halo$(C_{1-6})$-alkyl or —$(CH_2)_{0-3}$—$(C_{3-6})$-cycloalkyl;

or a stereoisomer, an isotopic form or a pharmaceutically acceptable salt thereof.

In another aspect, the present invention relates to the compound of formula (I), wherein: $R^1$ represents phenyl optionally substituted with one or more groups selected from halogen, $(C_{1-6})$-alkyl or halo$(C_{1-6})$-alkyl; or a stereoisomer or an isotopic form or a pharmaceutically acceptable salt thereof.

In another aspect, the present invention relates to the compound of formula (I), wherein $R^1$ represents pyridyl optionally substituted with one or more groups selected from halogen, $(C_{1-6})$-alkyl or halo$(C_{1-6})$-alkyl; or a stereoisomer, or an isotopic form, or a pharmaceutically acceptable salt thereof.

In another aspect, the present invention relates to the compound of formula (I), wherein: $R^1$ represents phenyl or a stereoisomer or an isotopic form or a pharmaceutically acceptable salt thereof.

In another aspect, the present invention relates to the compound of formula (I),

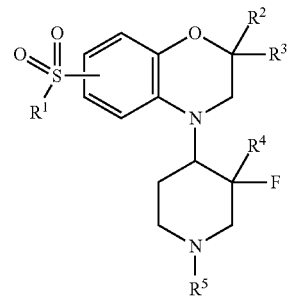

(I)

wherein:
$R^1$ represents phenyl optionally substituted with one or more groups selected from halogen, $(C_{1-6})$-alkyl or halo$(C_{1-6})$-alkyl;

$R^2$ represents hydrogen;

$R^3$ represents hydrogen;

$R^4$ represents hydrogen or $(C_{1-6})$-alkyl;

$R^5$ represents hydrogen;

or a stereoisomer, an isotopic form or a pharmaceutically acceptable salt thereof.

In another embodiment, the compound of the invention is selected from the group consisting of:

7-Phenylsulfonyl-4-(3-fluoropiperidin-4-yl)-3,4-dihydro-2H-benzo[1,4]oxazine;

7-(3-Fluorophenylsulfonyl)-4-(3-fluoropiperidin-4-yl)-3,4-dihydro-2H-benzo[1,4]oxazine;

4-(3-Fluoropiperidin-4-yl)-7-(pyridine-2-sulfonyl)-3,4-dihydro-2H-benzo[1,4]oxazine;

4-(3-Fluoropiperidin-4-yl)-7-(pyridine-4-sulfonyl)-3,4-dihydro-2H-benzo[1,4]oxazine;

7-Phenylsulfonyl-4-(3-fluoro-3-methylpiperidin-4-yl)-3,4-dihydro-2H-benzo[1,4]oxazine;

6-Phenylsulfonyl-4-(3-fluoropiperidin-4-yl)-3,4-dihydro-2H-benzo[1,4]oxazine; and 7-Phenylsulfonyl-4-[3-fluoro-1-(2-fluoroethyl)piperidin-4-yl]-3,4-dihydro-2H-benzo[1,4]oxazine;

or a stereoisomer or a pharmaceutically acceptable salt thereof.

In another embodiment, the preferred compound of the invention is selected from the group consisting of:
Racemic-7-Phenylsulfonyl-4-(3-fluoropiperidin-4-yl)-3,4-dihydro-2H-benzo[1,4]oxazine;
7-Phenylsulfonyl-4-(3-fluoropiperidin-4-yl)-3,4-dihydro-2H-benzo[1,4]oxazine (Peak I);
7-Phenylsulfonyl-4-(3-fluoropiperidin-4-yl)-3,4-dihydro-2H-benzo[1,4]oxazine (Peak II);
7-Phenylsulfonyl-4-(3-fluoropiperidin-4-yl)-3,4-dihydro-2H-benzo[1,4]oxazine (Peak III);
7-Phenylsulfonyl-4-(3-fluoropiperidin-4-yl)-3,4-dihydro-2H-benzo[1,4]oxazine (Peak IV);
7-Phenylsulfonyl-4-(3-fluoropiperidin-4-yl)-3,4-dihydro-2H-benzo[1,4]oxazine hydrochloride (Peak I);
7-Phenylsulfonyl-4-(3-fluoropiperidin-4-yl)-3,4-dihydro-2H-benzo[1,4]oxazine hydrochloride (Peak II);
7-Phenylsulfonyl-4-(3-fluoropiperidin-4-yl)-3,4-dihydro-2H-benzo[1,4]oxazine hydrochloride (Peak III);
7-Phenylsulfonyl-4-(3-fluoropiperidin-4-yl)-3,4-dihydro-2H-benzo[1,4]oxazine hydrochloride (Peak IV);
Racemic-7-(3-Fluorophenylsulfonyl)-4-(3-fluoropiperidin-4-yl)-3,4-dihydro-2H-benzo[1,4]oxazine;
7-(3-Fluorophenylsulfonyl)-4-(3-fluoropiperidin-4-yl)-3,4-dihydro-2H-benzo[1,4]oxazine (Peak I);
7-(3-Fluorophenylsulfonyl)-4-(3-fluoropiperidin-4-yl)-3,4-dihydro-2H-benzo[1,4]oxazine (Peak II);
7-(3-Fluorophenylsulfonyl)-4-(3-fluoropiperidin-4-yl)-3,4-dihydro-2H-benzo[1,4]oxazine (Peak III);
7-(3-Fluorophenylsulfonyl)-4-(3-fluoropiperidin-4-yl)-3,4-dihydro-2H-benzo[1,4]oxazine (Peak IV);
7-(3-Fluorophenylsulfonyl)-4-(3-fluoropiperidin-4-yl)-3,4-dihydro-2H-benzo[1,4]oxazine hydrochloride (Peak I);
7-(3-Fluorophenylsulfonyl)-4-(3-fluoropiperidin-4-yl)-3,4-dihydro-2H-benzo[1,4]oxazine hydrochloride (Peak II);
7-(3-Fluorophenylsulfonyl)-4-(3-fluoropiperidin-4-yl)-3,4-dihydro-2H-benzo[1,4]oxazine hydrochloride (Peak III);
7-(3-Fluorophenylsulfonyl)-4-(3-fluoropiperidin-4-yl)-3,4-dihydro-2H-benzo[1,4]oxazine hydrochloride (Peak IV);
Racemic-4-(3-Fluoropiperidin-4-yl)-7-(pyridine-2-sulfonyl)-3,4-dihydro-2H-benzo[1,4]oxazine;
Racemic-4-(3-Fluoropiperidin-4-yl)-7-(pyridine-2-sulfonyl)-3,4-dihydro-2H-benzo[1,4]oxazine hydrochloride;
Racemic-4-(3-Fluoropiperidin-4-yl)-7-(pyridine-4-sulfonyl)-3,4-dihydro-2H-benzo[1,4]oxazine;
Racemic-4-(3-Fluoropiperidin-4-yl)-7-(pyridine-4-sulfonyl)-3,4-dihydro-2H-benzo[1,4]oxazine hydrochloride;
Racemic-7-Phenylsulfonyl-4-(3-fluoro-3-methylpiperidin-4-yl)-3,4-dihydro-2H-benzo[1,4]oxazine;
7-Phenylsulfonyl-4-(3-fluoro-3-methylpiperidin-4-yl)-3,4-dihydro-2H-benzo[1,4]oxazine hydrochloride (First eluting isomer);
7-Phenylsulfonyl-4-(3-fluoro-3-methylpiperidin-4-yl)-3,4-dihydro-2H-benzo[1,4]oxazine hydrochloride (Second eluting isomer);
Racemic-6-Phenylsulfonyl-4-(3-fluoropiperidin-4-yl)-3,4-dihydro-2H-benzo[1,4]oxazine;
Racemic-6-Phenylsulfonyl-4-(3-fluoropiperidin-4-yl)-3,4-dihydro-2H-benzo[1,4]oxazine hydrochloride;
6-Phenylsulfonyl-4-(3-fluoropiperidin-4-yl)-3,4-dihydro-2H-benzo[1,4]oxazine (Peak I);
6-Phenylsulfonyl-4-(3-fluoropiperidin-4-yl)-3,4-dihydro-2H-benzo[1,4]oxazine (Peak II);
6-Phenylsulfonyl-4-(3-fluoropiperidin-4-yl)-3,4-dihydro-2H-benzo[1,4]oxazine (Peak III);
6-Phenylsulfonyl-4-(3-fluoropiperidin-4-yl)-3,4-dihydro-2H-benzo[1,4]oxazine (Peak IV);
7-Phenylsulfonyl-4-[3-fluoro-1-(2-fluoroethyl)piperidin-4-yl]-3,4-dihydro-2H-benzo[1,4]oxazine (Peak III);
7-Phenylsulfonyl-4-[3-fluoro-1-(2-fluoroethyl)piperidin-4-yl]-3,4-dihydro-2H-benzo[1,4]oxazine (Peak IV);
or a stereoisomer or an isotopic form or a pharmaceutically acceptable salt thereof.

In another embodiment, the preferred compound of the invention is selected from the group consisting of:
7-Phenylsulfonyl-4-(3-fluoropiperidin-4-yl)-3,4-dihydro-2H-benzo[1,4]oxazine hydrochloride (Peak III);
7-Phenylsulfonyl-4-(3-fluoropiperidin-4-yl)-3,4-dihydro-2H-benzo[1,4]oxazine hydrochloride (Peak I);
7-Phenylsulfonyl-4-(3-fluoropiperidin-4-yl)-3,4-dihydro-2H-benzo[1,4]oxazine hydrochloride (Peak II);
7-Phenylsulfonyl-4-(3-fluoropiperidin-4-yl)-3,4-dihydro-2H-benzo[1,4]oxazine hydrochloride (Peak IV);
7-(3-Fluorophenylsulfonyl)-4-(3-fluoropiperidin-4-yl)-3,4-dihydro-2H-benzo[1,4]oxazine hydrochloride (Peak I);
7-(3-Fluorophenylsulfonyl)-4-(3-fluoropiperidin-4-yl)-3,4-dihydro-2H-benzo[1,4]oxazine hydrochloride (Peak II);
7-(3-Fluorophenylsulfonyl)-4-(3-fluoropiperidin-4-yl)-3,4-dihydro-2H-benzo[1,4]oxazine hydrochloride (Peak III);
7-(3-Fluorophenylsulfonyl)-4-(3-fluoropiperidin-4-yl)-3,4-dihydro-2H-benzo[1,4]oxazine hydrochloride (Peak IV);
Racemic-4-(3-Fluoropiperidin-4-yl)-7-(pyridine-2-sulfonyl)-3,4-dihydro-2H-benzo[1,4]oxazine hydrochloride;
Racemic-4-(3-Fluoropiperidin-4-yl)-7-(pyridine-4-sulfonyl)-3,4-dihydro-2H-benzo[1,4]oxazine hydrochloride;
7-Phenylsulfonyl-4-(3-fluoro-3-methylpiperidin-4-yl)-3,4-dihydro-2H-benzo[1,4]oxazine hydrochloride (First eluting isomer);
7-Phenylsulfonyl-4-(3-fluoro-3-methylpiperidin-4-yl)-3,4-dihydro-2H-benzo[1,4]oxazine hydrochloride (Second eluting isomer);
Racemic-6-Phenylsulfonyl-4-(3-fluoropiperidin-4-yl)-3,4-dihydro-2H-benzo[1,4]oxazine hydrochloride;
6-Phenylsulfonyl-4-(3-fluoropiperidin-4-yl)-3,4-dihydro-2H-benzo[1,4]oxazine (Peak I);
6-Phenylsulfonyl-4-(3-fluoropiperidin-4-yl)-3,4-dihydro-2H-benzo[1,4]oxazine (Peak II);
6-Phenylsulfonyl-4-(3-fluoropiperidin-4-yl)-3,4-dihydro-2H-benzo[1,4]oxazine (Peak III);
6-Phenylsulfonyl-4-(3-fluoropiperidin-4-yl)-3,4-dihydro-2H-benzo[1,4]oxazine (Peak IV);
7-Phenylsulfonyl-4-[3-fluoro-1-(2-fluoroethyl)piperidin-4-yl]-3,4-dihydro-2H-benzo[1,4]oxazine (Peak III); and
7-Phenylsulfonyl-4-[3-fluoro-1-(2-fluoroethyl)piperidin-4-yl]-3,4-dihydro-2H-benzo[1,4]oxazine (Peak IV);
or a stereoisomer or an isotopic form or a pharmaceutically acceptable salt thereof.

Experimental Procedures

The scheme-1 depicts the general process for preparation of the compounds of formula (1), wherein $R^1$, $R^2$, $R^3$, $R^4$ and $R^5$ are as defined in the first aspect.

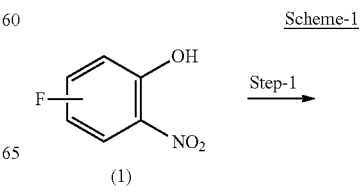

Scheme-1

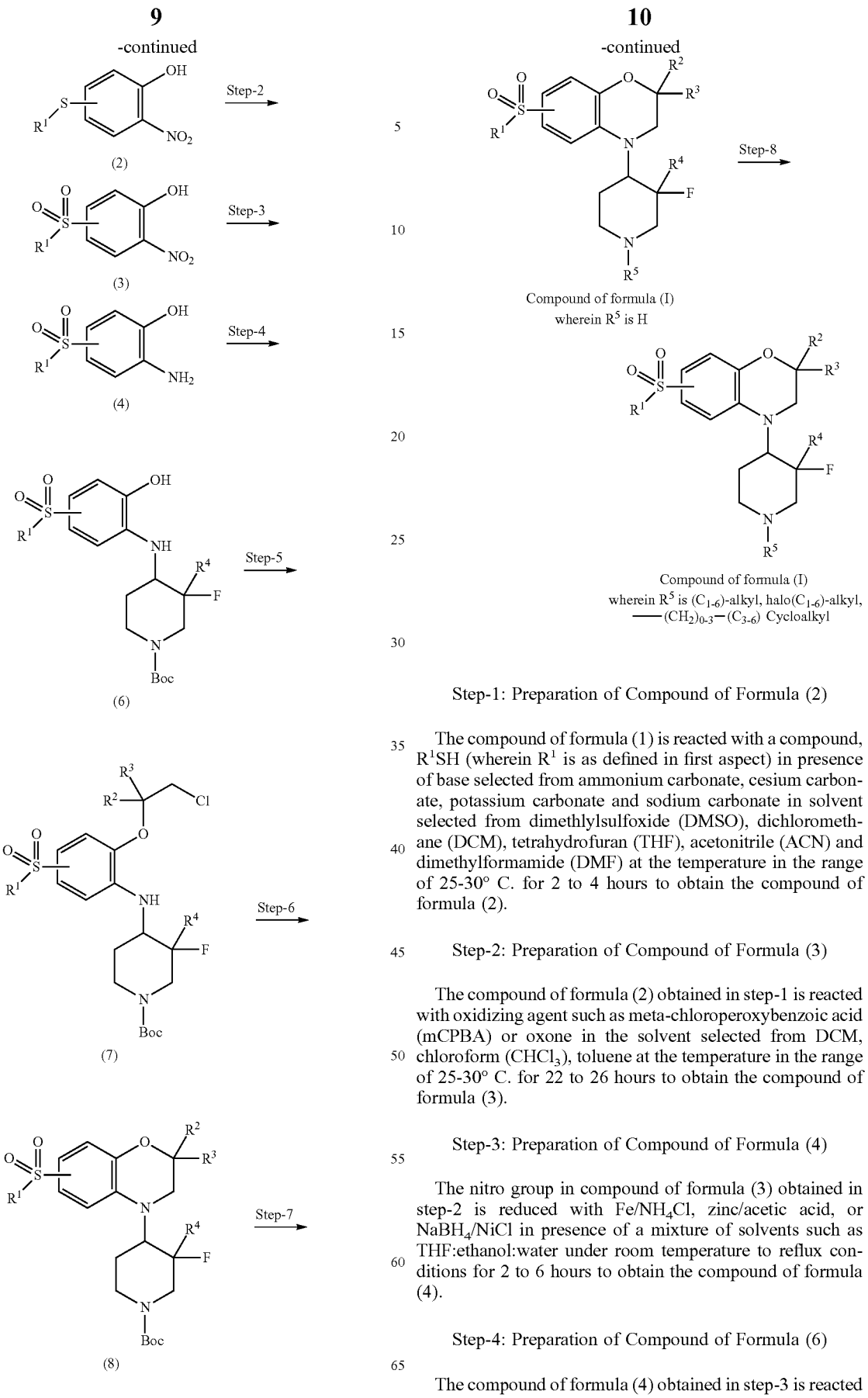

Step-1: Preparation of Compound of Formula (2)

The compound of formula (1) is reacted with a compound, $R^1SH$ (wherein $R^1$ is as defined in first aspect) in presence of base selected from ammonium carbonate, cesium carbonate, potassium carbonate and sodium carbonate in solvent selected from dimethlylsulfoxide (DMSO), dichloromethane (DCM), tetrahydrofuran (THF), acetonitrile (ACN) and dimethylformamide (DMF) at the temperature in the range of 25-30° C. for 2 to 4 hours to obtain the compound of formula (2).

Step-2: Preparation of Compound of Formula (3)

The compound of formula (2) obtained in step-1 is reacted with oxidizing agent such as meta-chloroperoxybenzoic acid (mCPBA) or oxone in the solvent selected from DCM, chloroform ($CHCl_3$), toluene at the temperature in the range of 25-30° C. for 22 to 26 hours to obtain the compound of formula (3).

Step-3: Preparation of Compound of Formula (4)

The nitro group in compound of formula (3) obtained in step-2 is reduced with $Fe/NH_4Cl$, zinc/acetic acid, or $NaBH_4/NiCl$ in presence of a mixture of solvents such as THF:ethanol:water under room temperature to reflux conditions for 2 to 6 hours to obtain the compound of formula (4).

Step-4: Preparation of Compound of Formula (6)

The compound of formula (4) obtained in step-3 is reacted with the compound of formula (5),

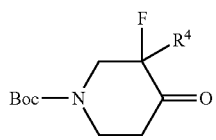

(5)

under reductive amination conditions using reducing agents such as sodium triacetoxyborohydride, sodium cyanoborohydride, sodium borohydride in the solvents selected from DCM, dichloroethane (EDC), CHCl$_3$, methanol, acetic acid and toluene at the temperature in the range of 25-30° C. for 22 to 26 hours to obtain the compound of formula (6).

Step-5: Preparation of Compound of Formula (7)

The compound of formula (6) obtained in step-4 is reacted with the compound of formula (A),

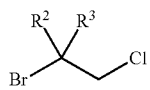

(A)

in presence of iodinating agents such as sodium iodide and tetrabutylammonium iodide and base such as potassium carbonate, sodium carbonate, cesium carbonate in the solvent selected from DCM, THF, ACN and DMF under room temperature to reflux conditions for 4 to 8 hours to obtain the compound of formula (7).

Step-6: Preparation of Compound of Formula (8)

The compound of formula (7) obtained in step-5 is cyclized using sodium iodide or tetra-butyl ammonium iodide and potassium carbonate, cesium carbonate, sodium hydride or sodium tert-butoxide in the solvent selected from THF, ACN and DMF at the temperature in the range of 25-30° C. for 2 to 6 hours to obtain the compound of formula (8).

Step-7: Preparation of Compound of Formula (I) (Wherein R$^5$ is Hydrogen)

The compound of formula (8) obtained in step-6 is subjected to tert-butyloxycarbonyl group removal using solvents such as methanol, ethanol, isopropanol, ethyl acetate, 1,4-dioxan and acid such as hydrochloric acid, hydrobromic acid, trifluoroacetic acid under room temperature to reflux conditions, for 2 to 6 hours, to obtain the compound of formula (I) (wherein R$^5$ is hydrogen).

Step-8: Preparation of Compound of Formula (I) (Wherein R$^5$ is (C$_{1-6}$)-alkyl, Halo(C$_{1-6}$)-alkyl or —(CH$_2$)$_{0-3}$—(C$_{3-6}$)-cycloalkyl)

The compound of formula (I) obtained in step-7 is optionally alkylated using formaldehyde/formic acid mixture, aldehydes, ketones, alkyl halides or cycloalkyl halides to obtain a compound of formula (I) (wherein R$^5$ is (C$_{1-6}$)-alkyl, halo(C$_{1-6}$)-alkyl or —(CH$_2$)$_{0-3}$—(C$_{3-6}$)-cycloalkyl).

Separation of Enantiomers

The diastereoisomers of compound of formula (8), compound of formula (I), are separated using chiral column chromatography separation to obtain the pure enantiomeric forms.

Preparation of Pharmaceutically Acceptable Salt of Compound of Formula (I)

The compound of formula (I) can optionally be converted into its pharmaceutically acceptable salt by reaction with the appropriate acid or acid derivative. Suitable pharmaceutically acceptable salts will be apparent to those skilled in the art. The salts are formed with inorganic acids e.g., hydrochloric, hydrobromic, sulfuric, perchloric & phosphoric acid or organic acids e.g., oxalic, succinic, maleic, acetic, fumaric, citric, malic, tartaric, benzoic, tolueic, toluenesulfonic, benzenesulfonic acid, methanesulfonic or naphthalenesulfonic acid.

Scheme-2 depicts the process for preparation of compound of formula (3a).

Scheme-2

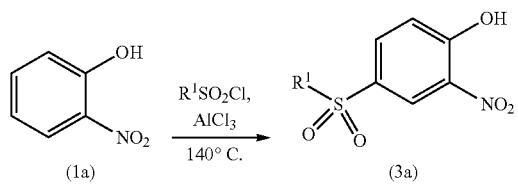

The compound of formula (Ia) is reacted with R$^1$SO$_2$Cl in presence of aluminum chloride at a temperature in the range of 130-150° C. for 8 to 16 hours to obtain compound of formula (3a). The compound of formula (3a) can also be converted into compound of formula (I) by following the process in scheme-1, starting from step-3.

Preparation of Stereoisomers of Compound of Formula (I)

The stereoisomers of compounds of formula (I) may be prepared by one or more conventional ways presented below:

a. One or more of the reagents may be used in their optically active form.
b. Optically pure catalyst or chiral ligands along with metal catalyst may be employed in the reduction process. The metal catalyst may be rhodium, ruthenium, indium and the like. The chiral ligands may preferably be chiral phosphines.
c. The mixture of stereoisomers may be resolved by conventional methods such as forming diastereomeric salts with chiral acids or chiral amines or chiral amino alcohols, or chiral amino acids. The resulting mixture of diastereomers may then be separated by methods such as fractional crystallization, chromatography and the like, which is followed by an additional step of isolating the optically active product from the resolved material/salt.
d. The mixture of stereoisomers may be resolved by conventional methods such as microbial resolution, resolving the diastereomeric salts formed with chiral acids or chiral bases. Chiral acids that can be employed may be tartaric acid, mandelic acid, lactic acid, camphorsulfonic acid, chiral amino acids and the like. Chiral bases that can be employed may be cinchona alkaloids, brucine or a basic amino acid such as lysine, arginine and the like.

In another embodiment, the suitable pharmaceutically acceptable salt includes but not limited to hydrochloride, hydrobromide, oxalate, fumarate, tartrate, maleate and succinate.

In another aspect of the present invention, the compound of formula (I) are 5-Hydroxytryptamine 6 receptor (5-HT6R) antagonists.

In another aspect, the present invention relates to a method of treatment of cognitive disorders comprising administering to a patient in need thereof, a therapeutically effective amount of compounds of formula (I) or a stereoisomer or an isotopic form or a pharmaceutically acceptable salt thereof.

In another aspect, the present invention relates to a method of treatment of cognitive disorders including dementia in Alzheimer's disease, dementia in Parkinson's disease, dementia in Huntington's disease, dementia associated with Down syndrome, dementia associated with Tourette's syndrome, dementia associated with post menopause, frontotemporal dementia, Lewy body dementia, Vascular dementia, dementia in HIV, dementia in Creutzfeldt-Jakob disease, substance-induced persisting dementia, dementia in Pick's disease, dementia in schizophrenia, dementia in general medical conditions and senile dementia comprising administering to a patient in need thereof, a therapeutically effective amount of compounds of formula (I) or a stereoisomer or an isotopic form or a pharmaceutically acceptable salt thereof.

In yet another aspect, the present invention relates to compound of formula (I) or a stereoisomer or an isotopic form or a pharmaceutically acceptable salt thereof, for use in the treatment of disease or disorder selected from cognitive disorders.

In yet another aspect, the present invention relates to use of the compound of formula (I) or a stereoisomer or an isotopic form or a pharmaceutically acceptable salt thereof, in the manufacture of medicament for the treatment of cognitive disorders.

In yet another aspect, the present invention relates to use of the compound of formula (I) or a stereoisomer or an isotopic form or a pharmaceutically acceptable salt thereof, in the manufacture of medicament for the treatment of cognitive disorders.

In yet another embodiment, the present invention relates to the combination of compound of formula (I) or a pharmaceutical salt thereof, an acetylcholinesterase inhibitor and a NMDA receptor antagonist, for use in the treatment of cognitive disorders.

In yet another embodiment, the present invention relates to the combination of compound of formula (I) or a pharmaceutical salt thereof and an acetylcholinesterase inhibitor, for use in the treatment of cognitive disorders.

In yet another embodiment, the present invention relates to the combination of compound of formula (I) or a pharmaceutical salt thereof and a NMDA receptor antagonist, for use in the treatment of cognitive disorders.

In another embodiment, the present invention relates to the combination wherein the acetylcholinesterase inhibitor is selected from galantamine, rivastigmine, donepezil and tacrine or a pharmaceutically acceptable salt thereof.

In another embodiment, the present invention relates to the combination wherein the acetylcholinesterase inhibitor in the combination is donepezil hydrochloride.

In another embodiment, the present invention relates to the combination wherein the NMDA receptor antagonist in the combination is memantine or a pharmaceutically acceptable salt thereof. In another embodiment, the present invention relates to the combination wherein the NMDA receptor antagonist in the combination is memantine hydrochloride.

In yet another aspect, the present invention relates to the pharmaceutical composition of the compound of formula (I).

In order to use the compound of formula (I), or their stereoisomers and pharmaceutically acceptable salts thereof in therapy, they will normally be formulated into a pharmaceutical composition in accordance with standard pharmaceutical practice.

The pharmaceutical compositions of the present invention may be formulated in a conventional manner using one or more pharmaceutically acceptable excipients. The pharmaceutically acceptable excipients are diluents, disintegrants, binders, lubricants, glidants, polymers, coating agents, solvents, cosolvents, preservatives, wetting agents, thickening agents, antifoaming agents, sweetening agents, flavouring agents, antioxidants, colorants, solubilizers, plasticizer, dispersing agents and the like. Excipients are selected from microcrystalline cellulose, mannitol, lactose, pregelatinized starch, sodium starch glycolate, corn starch or derivatives thereof, povidone, crospovidone, calcium stearate, glyceryl monostearate, glyceryl palmitostearate, talc, colloidal silicone dioxide, magnesium stearate, sodium lauryl sulfate, sodium stearyl fumarate, zinc stearate, stearic acid or hydrogenated vegetable oil, gum arabica, magnesia, glucose, fats, waxes, natural or hardened oils, water, physiological sodium chloride solution or alcohols, for example, ethanol, propanol or glycerol, sugar solutions, such as glucose solutions or mannitol solutions and the like or a mixture of the various excipients.

In yet another aspect, the active compounds of the invention may be formulated in the form of pills, tablets, coated tablets, capsules, powder, granules, pellets, patches, implants, films, liquids, semi-solids, gels, aerosols, emulsions, elixirs and the like. Such pharmaceutical compositions and processes for preparing same are well known in the art. In yet another aspect, the pharmaceutical composition of the instant invention contains 1 to 90%, 5 to 75% and 10 to 60% by weight of the compounds of the instant invention or pharmaceutically acceptable salt thereof. The amount of the active compounds or its pharmaceutically acceptable salt in the pharmaceutical composition(s) can range from about 1 mg to about 500 mg or from about 5 mg to about 400 mg or from about 5 mg to about 250 mg or from about 7 mg to about 150 mg or in any range falling within the broader range of 1 mg to 500 mg.

The dose of the active compounds can vary depending on factors such as age and weight of patient, nature and severity of the disease to be treated and such other factors. Therefore, any reference regarding pharmacologically effective amount of the compounds of general formula (I), stereoisomers and pharmaceutically acceptable salts thereof refers to the aforementioned factors.

ABBREVIATIONS

The following abbreviations are used herein:
5-HT: 5-Hydroxytryptamine
$5\text{-HT}_6$: 5-Hydroxytryptamine 6
$5\text{-HT}_{2A}$: 5-Hydroxytryptamine 2A
ACN: Acetonitrile
$AlCl_3$: Aluminum chloride
AUC: Area under the curve
$C_{max}$: Maximum concentration
CSF: Cerebrospinal fluid
$CHCl_3$: Chloroform
$CDCl_3$: Deuterated chloroform
$Cs_2CO_3$: Cesium carbonate
$CD_3OD$: Deuterated methanol
DCM: Dichloromethane
DEA: Diethylamine DMF: N,N-Dimethylformamide
DMSO: Dimethyl sulfoxide
EDC: Ethylene dichloride
EDTA: Ethylenediaminetetraacetic acid
Fe: Iron
g: Grams
$H_2O$: Water
HCl: Hydrochloric acid
IPA: Isopropyl alcohol
$K_b$: Binding constant
$K_i$: Inhibitory constant
LC-MS/MS: Liquid chromatography-Mass spectrometry/Mass spectrometry
MeOH: Methanol
$NaBH_4$: Sodium borohydride
NaI: Sodium iodide
$NaIO_4$: Sodium periodate
$NaHCO_3$: Sodium bicarbonate
NiCl: Nickel chloride
$Na_2SO_4$: Sodium sulphate
$NaBH(OAc)_3$: Sodium triacetoxyborohydride
$NH_3$: Ammonia
NMDA: N-methyl-D-aspartate
p.o.: Per oral
RT: Retention Time
ROA: Route of Administration
THF: Tetrahydrofuran
m-CPBA: meta-chloro perbenzoic acid
$NaBH(OAc)_3$: Sodium triacetoxyborohydride
h: Hour (s)
i.v.: Intravenous
NOAEL: No Observed Adverse Effect Level
ng: Nanogram
mg: Milligram
s.c.: Sub cutaneous
$T_{1/2}$: Half-life time

EXAMPLES

The compounds of the present invention were prepared according to the following experimental procedures, using appropriate materials and conditions. The following examples are provided by way of illustration only but not to limit the scope of present invention.

Intermediate 1: 2-Nitro-5-(phenylsulfanyl) phenol

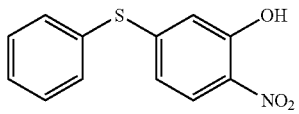

$Cs_2CO_3$ (78 g, 0.24 mole) was added in portions to a stirred solution of 5-fluoro-2-nitro phenol (31.4 g, 0.2 mole) and thiophenol (24.2 g, 0.22 mole) in DMF (600 mL) at 25-35° C. The resulting mass was stirred for 1 hour at room temperature, poured on to cold water (1000 mL) during which solids precipitated. These solids were filtered and dissolved in $CHCl_3$ (1000 mL). The organic layer was washed with brine (250 mL), dried over anhydrous $Na_2SO_4$, filtered and concentrated on rotavap to obtain crude mass which was purified by column chromatography using ethyl acetate: n-hexane (30:70) to obtain 2-nitro-5-(phenylsulfanyl)phenol.

Yield: 47.2 g (95%); $^1$H-NMR ($CDCl_3$, 400 MHz) δ ppm: 6.67-6.68 (m, 2H), 7.47-7.52 (m, 3H), 7.55-7.58 (m, 2H), 7.93-7.95 (d, J=9.52 Hz, 1H), 10.7 (s, 1H); Mass (m/z): 247.9 (M+H)$^+$.

Intermediate 2: 5-(Phenylsulfonyl)-2-nitro phenol

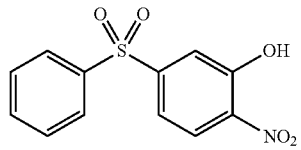

m-CPBA (82.4 g, 0.47 mole) was added in portions to a stirred solution of 2-nitro-5-(phenylsulfanyl) phenol (47 g, 0.19 mole) in DCM (1000 mL) at room temperature (exothermic, mild reflux of solvent). The reaction mixture was further stirred for 18 hours at room temperature and poured on to water (500 mL). The organic layer was separated, washed with 10% aqueous $NaHCO_3$ solution (250 mL×2), brine (250 mL), dried over anhydrous $Na_2SO_4$, filtered and concentrated on rotavap to obtain 5-phenylsulfonyl-2-nitro phenol.

Yield: 52.2 g (~100%); $^1$H-NMR ($CDCl_3$, 400 MHz) δ ppm: 7.49-7.52 (dd, J=1.52, 8.76 Hz, 1H), 7.55-7.58 (m, 2H), 7.63-7.67 (m, 1H), 7.76-7.76 (d, J=1.36 Hz, 1H), 7.96-7.98 (d, J=7.48 Hz, 2H), 8.22-8.24 (d, J=8.84 Hz, 1H), 10.58 (s, 1H); Mass (m/z): 278.2 (M–H)$^+$.

Intermediate 3: 2-Amino-5-(phenylsulfonyl) phenol

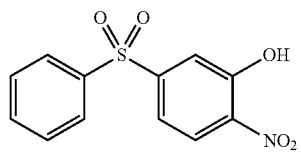

A suspension of 5-(phenylsulfonyl)-2-nitro phenol (52 g, 0.18 mole), Fe (41 g, 0.74 mole) and $NH_4Cl$ (49.8 g, 0.93 mole) in $H_2O$, ethanol (D.S) and THF (1000 mL:250 mL:250 mL) was refluxed for ~4 h. The reaction mixture was cooled to room temperature and concentrated to obtain a residual mass. Water (500 mL) was added to the above mixture and basified with $NaHCO_3$ (pH-9) and the product was extracted with $CHCl_3$ (500 mL×3). The organic extracts were combined, washed with brine (250 mL), dried over anhydrous $Na_2SO_4$, filtered and concentrated on rotavap to obtain 2-amino-5-(phenylsulfonyl) phenol.

Yield: 41.7 g (~90%); $^1$H-NMR ($CD_3OD$, 400 MHz) δ ppm: 6.71-6.71 (m, 1H), 7.13-7.22 (m, 2H), 7.51-7.53 (m, 3H), 7.83-7.85 (m, 2H); Mass (m/z): 250.1 (M+H)$^+$.

Intermediate 4: tert-Butyl 4-(4-phenylsulfonyl-2-hydroxy phenylamino)-3-fluoropiperidin-1-carboxylate

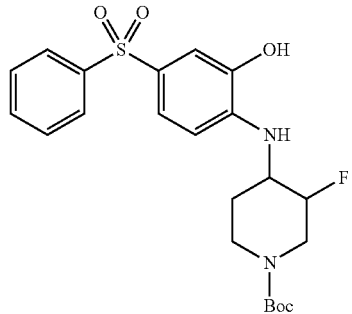

A suspension of 2-amino-5-(phenylsulfonyl) phenol (40 g, 0.16 mole), tert-butyl 3-fluoro-4-oxo-piperidin-1-carboxylate (41.8 g, 0.19 mole) in EDC (1000 mL) was refluxed for 4 h to obtain a clear solution. The reaction mixture was cooled to room temperature and NaBH(OAc)$_3$ (102 g, 0.48 mole) was added to above solution in three equal lots, each in 1 h time interval. The reaction mixture was stirred for 18 h at room temperature, and again refluxed for 1 h. The reaction mixture was cooled to room temperature, added water (500 mL), and basified with aq. NH$_3$ solution (pH-9). The organic layer was separated and aqueous layer was extracted with ethyl acetate (500 mL×3). The organic extracts were combined, washed with brine (250 mL), dried over anhydrous Na$_2$SO$_4$, filtered and concentrated on rotavap to obtain crude mass which was purified by column chromatography using ethyl acetate: n-hexane (30:70) to obtain tert-butyl 4-(4-phenylsulfonyl-2-hydroxy phenylamino)-3-fluoro piperidin-1-carboxylate as a diastereomeric mixture.

Yield: 60.3 g (~83%); HPLC (55.5% and 40.8%); diastereomeric pair; Mass (m/z): 449.4 (M–H)$^+$.

Intermediate 5: tert-Butyl 4-[4-phenylsulfonyl-2-(2-chloroethoxy) phenylamino]-3-fluoropiperidin-1-carboxylate

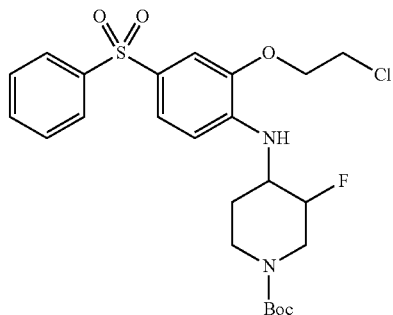

Potassium carbonate (73.5 g, 0.53 mole) was added to a stirred mixture of tert-butyl 4-(4-phenylsulfonyl-2-hydroxy phenylamino)-3-fluoro piperidin-1-carboxylate (60 g, 0.13 mole), 1-bromo-2-chloroethane and NaI (2 g, 0.013 mole) in acetonitrile (1000 mL). The reaction mixture was refluxed for 5 h, cooled to room temperature, poured on to water (1000 mL) and extracted with ethyl acetate (1000 mL×2). The organic extracts were combined, dried over anhydrous Na$_2$SO$_4$, filtered and concentrated on rotavap to obtain crude mass which was purified by column chromatography. First eluting diastereomer (along with some second eluting isomer) was obtained in ethyl acetate:CHCl$_3$ (3:97) and the second eluting diastereomer (along with some first eluting isomer) was obtained in ethyl acetate:CHCl$_3$ (5:95 and then ethyl acetate was increased in gradient).

First Eluting Isomer:
Yield: 12.74 g (~18.6%); HPLC 85.5%; $^1$H-NMR (CDCl$_3$, 400 MHz) δ ppm: 1.49 (s, 9H), 1.53-1.59 (m, 1H), 2.13-2.16 (m, 1H), 3.12-3.25 (m, 2H), 3.62-3.65 (m, 1H), 3.85-3.88 (m, 2H), 4.11-4.15 (m, 1H), 4.31-4.34 (m, 3H), 4.45-4.46 (m, 1H), 4.92-4.94 (d, J=7.38 Hz, 1H), 6.74-6.76 (d, J=8.58 Hz, 1H), 7.24-7.25 (m, 1H), 7.46-7.54 (m, 4H), 7.89-7.91 (d, J=7.26 Hz, 2H); Mass (m/z): 513.6, 515.5 (M+H)$^+$.

Second Eluting Isomer:
Yield: 24.69 g (~36%); HPLC 91.5%; $^1$H-NMR (CDCl$_3$, 400 MHz) δ ppm: 1.49 (s, 9H), 1.79-1.87 (m, 2H), 2.86-3.12 (m, 2H), 3.55-3.62 (m, 1H), 3.84-3.87 (m, 2H), 4.12-4.17 (m, 1H), 4.30-4.33 (m, 2H), 4.41-4.53 (m, 1H), 4.69-4.92 (m, 1H), 5.13-5.15 (d, J=9.12 Hz, 1H), 6.59-6.61 (d, J=8.46 Hz, 1H), 7.27-7.29 (m, 1H), 7.47-7.56 (m, 4H), 7.90-7.91 (d, J=7.1 Hz, 2H); Mass (m/z): 513.4, 515.2 (M+H)$^+$.

Intermediate 6: tert-Butyl 4-(7-phenylsulfonyl-2,3-dihydrobenzo[1,4]oxazin-4-yl)-3-fluoropiperidin-1-carboxylate

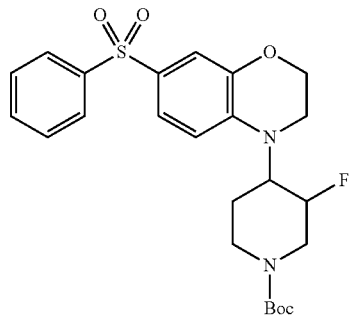

Sodium hydride (2.6 g, 0.064 mole, 60% dispersion in mineral oil) was added in portions to a stirred mixture of tert-butyl 4-[4-phenylsulfonyl-2-(2-chloroethoxy) phenylamino]-3-fluoro piperidin-1-carboxylate (second eluting isomer, 22 g, 0.04 mole) and NaI (0.32 g, 0.002 mole) in DMF (220 mL) at room temperature and stirred for 18 hours. The reaction mixture was then poured on to water (500 mL) and extracted with CHCl$_3$ (300 mL×3). The organic extracts were combined, washed with brine (50 mL), dried over anhydrous Na$_2$SO$_4$, filtered and concentrated on rotavap to obtain tert-butyl 4-(7-phenylsulfonyl-2,3-dihydro benzo[1,4]oxazin-4-yl)-3-fluoro piperidin-1-carboxylate as off white solids. These solids were triturated with n-hexane (100 mL×3) and the product was dried in vacuum on rotavap.

Yield: 18.3 g (~89%); HPLC (90.1%); $^1$H-NMR (CDCl$_3$, 400 MHz) δ ppm: 1.47 (s, 9H), 1.64-1.65 (m, 1H), 2.21-2.31 (m, 1H), 2.82-3.05 (m, 2H), 3.37-3.47 (m, 1H), 3.54-3.57 (m, 1H), 3.78-3.89 (m, 2H), 4.12-4.18 (m, 2H), 4.42-4.59 (m, 2H), 4.78-4.90 (m, 1H), 6.58-6.60 (d, J=8.74 Hz, 1H), 7.31-7.31 (d, J=1.94 Hz, 1H), 7.41-7.51 (m, 4H), 7.89-7.90 (d, J=7.21 Hz, 2H); Mass (m/z): 477.2 (M+H)⁺.

Intermediate 7: Chiral separation of tert-butyl 4-(7-phenylsulfonyl-2,3-dihydrobenzo[1,4]oxazin-4-yl)-3-fluoropiperidin-1-carboxylate Intermediate 6 (having 10% minor fraction and 90% major fraction as per HPLC) was separated by chiral column chromatography to Intermediate 7 as four separate peaks, using the method given below.

Method: Column ID: CHIRALPAK IC, Mobile Phase: DCM:Ethyl acetate (75:25), Flow rate: 1 mL/min, Temp: 25° C., Wavelength: 320 nM.

Intermediate 7 (Peak I): Chiral HPLC 99.9%, (RT: 8.6 min); ¹H-NMR (CDCl₃, 400 MHz) δ ppm: 1.47 (s, 9H), 1.61-1.68 (m, 2H), 1.82-1.86 (m, 1H), 2.78-2.84 (m, 2H), 3.34-3.44 (m, 2H), 3.88-3.91 (m, 1H), 4.16-4.22 (m, 3H), 4.57-4.62 (m, 1H), 6.77-6.79 (d, J=8.76 Hz, 1H), 7.31-7.31 (d, J=1.72 Hz, 1H), 7.42-7.52 (m, 4H), 7.88-7.90 (d, J=7.48 Hz, 2H); Mass (m/z): 477.3 (M+H)⁺.

Intermediate 7 (Peak II): Chiral HPLC 99.8%, (RT: 10.7 min); ¹H-NMR (CDCl₃, 400 MHz) δ ppm: 1.47 (s, 9H), 1.61-1.68 (m, 2H), 1.82-1.86 (m, 1H), 2.78-2.84 (m, 2H), 3.34-3.44 (m, 2H), 3.88-3.91 (m, 1H), 4.16-4.22 (m, 3H), 4.57-4.62 (m, 1H), 6.77-6.79 (d, J=8.76 Hz, 1H), 7.31-7.31 (d, J=1.72 Hz, 1H), 7.42-7.52 (m, 4H), 7.88-7.90 (d, J=7.48 Hz, 2H); Mass (m/z): 477.5 (M+H)⁺.

Intermediate 7 (Peak III): Chiral HPLC 99.9%, (RT: 12.2 min); ¹H-NMR (CDCl₃, 400 MHz) δ ppm: 1.47 (s, 9H), 1.62-1.64 (m, 1H), 2.24-2.28 (m, 1H), 2.84-3.01 (m, 2H), 3.42-3.47 (m, 1H), 3.54-3.58 (m, 1H), 3.76-3.87 (m, 1H), 4.14-4.19 (m, 2H), 4.43-4.50 (m, 2H), 4.78-4.91 (m, 1H), 6.58-6.60 (d, J=8.74 Hz, 1H), 7.31-7.32 (d, J=1.70 Hz, 1H), 7.41-7.53 (m, 4H), 7.89 7.91 (d, J=7.31 Hz, 2H); Mass (m/z): 477.1 (M+H)⁺.

Intermediate 7 (Peak IV): Chiral HPLC 99.7%, (RT: 17.8 min); ¹H-NMR (CDCl₃, 400 MHz) δ ppm: 1.47 (s, 9H), 1.62-1.64 (m, 1H), 2.24-2.28 (m, 1H), 2.84-3.01 (m, 2H), 3.42-3.47 (m, 1H), 3.54-3.58 (m, 1H), 3.76-3.87 (m, 1H), 4.14-4.19 (m, 2H), 4.43-4.50 (m, 2H), 4.78-4.91 (m, 1H), 6.58-6.60 (d, J=8.74 Hz, 1H), 7.31-7.32 (d, J=1.70 Hz, 1H), 7.41-7.53 (m, 4H), 7.89 7.91 (d, J=7.31 Hz, 2H); Mass (m/z): 477.1 (M+H)⁺.

Example 1

7-Phenylsulfonyl-4-(3-fluoropiperidin-4-yl)-3,4-dihydro-2H-benzo[1,4]oxazine hydrochloride (Peak III)

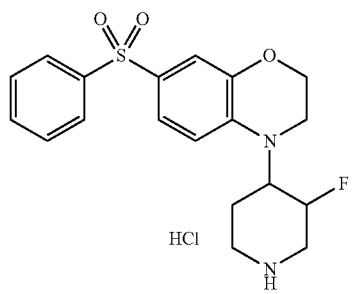

Methanolic HCl (16% w/v solution, 1.3 mL, 0.005 mole) was added to a stirred suspension of tert-butyl (4-(7-phenylsulfonyl-2,3-dihydro benzo[1,4]oxazin-4-yl)-3-fluoro piperidin-1-carboxylate (Intermediate 7 (Peak III), 0.5 g, 0.001 mole) in methanol (10 mL) and the resulting mixture was refluxed for ~4 h to obtain a clear solution. The reaction mixture was cooled to room temperature and concentrated in vacuum on rotavapor to obtain crystalline solid.

Yield: 0.41 g (95%); ¹H-NMR (DMSO-d₆, 400 MHz) δ ppm: 1.81-1.84 (m, 1H), 2.24-2.32 (m, 1H), 3.10-3.16 (m, 1H), 3.36-3.41 (m, 2H), 3.46-3.53 (m, 3H), 4.09-4.18 (m, 2H), 4.32-4.38 (m, 1H), 5.05-5.17 (d, J=47.8 Hz, 1H), 7.04-7.06 (d, J=8.89 Hz, 1H), 7.17-7.18 (d, J=2.05 Hz, 1H), 7.33-7.36 (m, 1H), 7.55-7.65 (m, 3H), 7.88-7.89 (d, J=7.4 Hz, 2H), 8.73 (bs, 1H), 9.52 (bs, 1H); Mass (m/z): 377.0 (M+H)⁺; HPLC (% purity): 99.93.

Example 2

7-Phenylsulfonyl-4-(3-fluoropiperidin-4-yl)-3,4-dihydro-2H-benzo[1,4]oxazine hydrochloride (Peak I)

The title compound was prepared from tert-butyl 4-(7-phenylsulfonyl-2,3-dihydrobenzo[1,4]oxazin-4-yl)-3-fluoropiperidin-1-carboxylate (Intermediate 7 (Peak I)) by following the experimental procedure of Example 1.

¹H-NMR (DMSO-d₆, 400 MHz) δ ppm: 1.87-1.90 (m, 1H), 1.97-2.09 (m, 1H), 3.04-3.10 (m, 2H), 3.37-3.39 (m, 3H), 3.63-3.66 (m, 1H), 4.14-4.18 (m, 2H), 4.46-4.48 (m, 1H), 5.00-5.15 (m, 1H), 7.07-7.11 (d, J=8.84 Hz, 1H), 7.15-7.16 (d, J=1.69 Hz, 1H), 7.34-7.36 (dd, J=1.27, 8.7 Hz, 1H), 7.55-7.65 (m, 3H), 7.87-7.89 (d, J=7.38 Hz, 2H), 8.56 (bs, 1H), 9.38 (bs, 1H); Mass (m/z): 377.2 (M+H)⁺; HPLC (% purity): 99.96.

Example 3

7-Phenylsulfonyl-4-(3-fluoropiperidin-4-yl)-3,4-dihydro-2H-benzo[1,4]oxazine hydrochloride (Peak II)

The title compound was prepared from tert-butyl 4-(7-phenylsulfonyl-2,3-dihydrobenzo[1,4]oxazin-4-yl)-3-fluoropiperidin-1-carboxylate (Intermediate 7 (Peak II)) by following the experimental procedure of Example 1.

¹H-NMR (DMSO-d₆, 400 MHz) δ ppm: 1.89-1.90 (m, 1H), 1.99-2.02 (m, 1H), 3.07-3.16 (m, 2H), 3.39-3.40 (m, 3H), 3.64-3.66 (m, 1H), 4.13-4.19 (m, 2H), 4.46-4.48 (m, 1H), 5.13-5.15 (m, 1H), 7.09-7.11 (d, J=8.91 Hz, 1H), 7.15-7.16 (d, J=2.61 Hz, 1H), 7.34-7.36 (dd, J=1.76, 8.75 Hz, 1H), 7.55-7.65 (m, 3H), 7.87-7.89 (d, J=7.4 Hz, 2H), 8.53 (bs, 1H), 9.34 (bs, 1H); Mass (m/z): 377.2 (M+H)⁺; HPLC (% purity): 94.00.

Example 4

7-Phenylsulfonyl-4-(3-fluoropiperidin-4-yl)-3,4-dihydro-2H-benzo[1,4]oxazine hydrochloride (Peak IV)

The title compound was prepared from tert-butyl 4-(7-phenylsulfonyl-2,3-dihydrobenzo[1,4]oxazin-4-yl)-3-fluoropiperidin-1-carboxylate (Intermediate 7 (Peak IV)) by following the experimental procedure of Example 1.

¹H-NMR (DMSO-d₆, 400 MHz) δ ppm: 1.81-1.84 (m, 1H), 2.27-2.34 (m, 1H), 3.12-3.15 (m, 1H), 3.37-3.52 (m, 5H), 4.10-4.16 (m, 2H), 4.31-4.37 (m, 1H), 5.05-5.17 (d, J=47.8 Hz, 1H), 7.05-7.07 (d, J=8.86 Hz, 1H), 7.17-7.17 (d, J=1.99 Hz, 1H), 7.33-7.35 (dd, J=1.87, 8.66 Hz, 1H), 7.56-7.63 (m, 3H), 7.87-7.89 (d, J=7.38 Hz, 2H), 8.68 (bs, 1H), 9.66 (bs, 1H); Mass (m/z): 377.2 (M+H)+; HPLC (% purity): 99.63.

Examples 5 to 8

The compounds of examples 5 to 8 were prepared by following the experimental procedures as described in the examples 1 to 4, with some non-critical variations using appropriate intermediates.

Example 5

7-(3-Fluorophenylsulfonyl)-4-(3-fluoropiperidin-4-yl)-3,4-dihydro-2H-benzo[1,4]oxazine hydrochloride (Peak I)

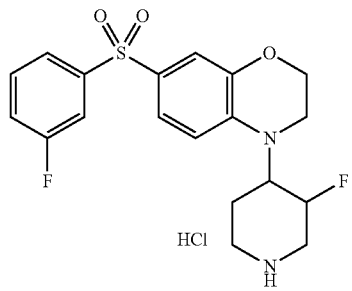

$^1$H-NMR (DMSO-$d_6$, 400 MHz) δ ppm: 1.90-2.01 (m, 2H), 3.05-3.15 (m, 3H), 3.34-3.39 (m, 2H), 3.64-3.67 (m, 1H), 4.12-4.19 (m, 2H), 4.45-4.49 (m, 1H), 4.94-5.13 (m, 1H), 7.08-7.10 (d, J=8.90 Hz, 1H), 7.20-7.21 (d, J=2.09 Hz, 1H), 7.37-7.40 (dd, J=2.04, 8.75 Hz, 1H), 7.49-7.51 (m, 1H), 7.61-7.65 (m, 1H), 7.71-7.75 (m, 2H), 9.09 (bs, 1H), 9.29 (bs, 1H); Mass (m/z): 395.2 (M+H)+; HPLC (% purity): 99.8.

Example 6

7-(3-Fluorophenylsulfonyl)-4-(3-fluoropiperidin-4-yl)-3,4-dihydro-2H-benzo[1,4]oxazine hydrochloride (Peak II)

$^1$H-NMR (DMSO-$d_6$, 400 MHz) δ ppm: 1.90-2.01 (m, 2H), 3.06-3.15 (m, 3H), 3.35-3.39 (m, 2H), 3.64-3.67 (m, 1H), 4.12-4.19 (m, 2H), 4.45-4.50 (m, 1H), 4.94-5.10 (m, 1H), 7.08-7.10 (d, J=9.8 Hz, 1H), 7.20-7.21 (d, J=2.02 Hz, 1H), 7.37-7.40 (dd, J=2.02, 8.74 Hz, 1H), 7.46-7.51 (m, 1H), 7.59-7.64 (m, 1H), 7.71-7.75 (m, 2H), 9.09 (bs, 1H), 9.29 (bs, 1H); Mass (m/z):395.2 (M+H)+; HPLC (% purity): 99.8.

Example 7

7-(3-Fluorophenylsulfonyl)-4-(3-fluoropiperidin-4-yl)-3,4-dihydro-2H-benzo[1,4]oxazine hydrochloride (Peak III)

$^1$H-NMR (DMSO-$d_6$, 400 MHz) δ ppm: 1.81-1.84 (m, 1H), 2.17-2.31 (m, 1H), 3.12-3.15 (m, 1H), 3.31-3.36 (m, 2H), 3.46-3.57 (m, 3H), 4.11-4.17 (m, 2H), 4.29-4.40 (m, 1H), 5.50-5.17 (d, J=47.68 Hz, 1H), 7.02-7.04 (d, J=8.87 Hz, 1H), 7.22-7.22 (d, J=1.69 Hz, 1H), 7.37-7.39 (dd, J=1.52, 8.68 Hz, 1H), 7.47-7.51 (m, 1H), 7.60-7.65 (m, 1H), 7.72-7.76 (m, 2H), 8.45-8.68 (bs, 1H), 9.36 (bs, 1H); Mass (m/z): 395.2 (M+H)+; HPLC (% purity): 99.39.

Example 8

7-(3-Fluorophenylsulfonyl)-4-(3-fluoropiperidin-4-yl)-3,4-dihydro-2H-benzo[1,4]oxazine hydrochloride (Peak IV)

$^1$H-NMR (DMSO-$d_6$, 400 MHz) δ ppm: 1.81-1.84 (m, 1H), 2.25-2.31 (m, 1H), 3.11-3.13 (m, 1H), 3.32-3.36 (m, 2H), 3.46-3.57 (m, 3H), 4.13-4.14 (m, 2H), 4.28-4.40 (m, 1H), 5.05-5.17 (d, J=47.71 Hz, 1H), 7.01-7.03 (d, J=8.74 Hz, 1H). 7.22-7.22 (d, J=1.65 Hz, 1H), 7.37-7.39 (m, 1H), 7.47-7.51 (m, 1H), 7.59-7.65 (m, 1H), 7.72-7.76 (m, 2H), 8.66 (bs, 1H), 9.24 (bs, 1H); Mass (m/z): 395.2 (M+H)+; HPLC (% purity): 98.78.

Example 9

Racemic-4-(3-Fluoropiperidin-4-yl)-7-(pyridine-2-sulfonyl)-3,4-dihydro-2H-benzo[1,4]oxazine hydrochloride

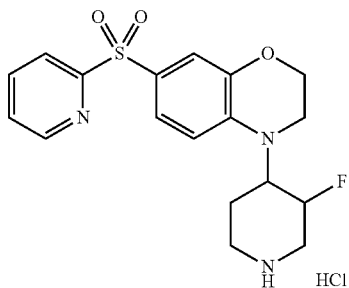

Step-1: 2-Nitro-5-(pyridin-2-sulfonyl)phenol

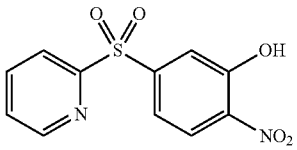

NaIO$_4$ (29 g, 0.13 mole) was added to a stirred mixture of 2-nitro-5-(pyridin-2-ylsulfanyl) phenol (6.8 g, 0.027 mole) in IPA:H$_2$O (100 mL:200 mL) and the reaction mixture was refluxed for 24 h. The reaction mixture was then cooled to room temperature, extracted using DCM (150 mL×3). The organic extracts were combined, dried over anhydrous Na$_2$SO$_4$, filtered and concentrated on rotavap to obtain crude mass which was purified by column chromatography using ethyl acetate: n-hexane (30:70) to obtain 2-nitro-5-(pyridin-2-sulfonyl)-phenol.

Yield: 6.2 g (81%); $^1$H-NMR (DMSO-$d_6$, 400 MHz) δ ppm: 7.45-7.48 (m, 1H), 7.69-7.75 (m, 2H), 8.02-8.04 (d, J=8.56 Hz, 1H), 8.16-8.28 (m, 2H), 8.72-8.73 (d, J=4.2 Hz, 1H), 11.96 (bs, 1H); Mass (m/z): 279.2 (M−H)+.

Racemic-4-(3-Fluoropiperidin-4-yl)-7-(pyridine-2-sulfonyl)-3,4-dihydro-2H-benzo[1,4]oxazine hydrochloride The title compound was synthesized by following the experimental procedures as described in intermediates 4 to 6, with some non-critical variations using 2-nitro-5-(pyridin-2-sulfonyl) phenol (obtained in above step) and appropriate intermediates.

$^1$H-NMR (DMSO-d$_6$, 400 MHz) δ ppm: 1.82-1.85 (m, 1H), 2.24-2.32 (m, 1H), 3.11-3.15 (m, 2H), 3.47-3.53 (m, 4H), 4.09-4.18 (m, 2H), 4.30-4.39 (m, 1H), 5.06-5.18 (d, J=47.81 Hz, 1H), 7.04-7.07 (d, J=8.86 Hz, 1H), 7.17-7.17 (d, J=2 Hz, 1H), 7.33-7.36 (dd, J=1.84, 8.68 Hz, 1H), 7.61-7.64 (m, 1H), 8.06-8.11 (m, 2H), 8.66-8.70 (m, 2H), 9.49 (bs, 1H); Mass (m/z): 378.2 (M+H)$^+$; HPLC (% purity): 97.54.

Example 10

Racemic-4-(3-Fluoropiperidin-4-yl)-7-(pyridine-4-sulfonyl)-3,4-dihydro-2H-benzo[1,4]oxazine hydrochloride

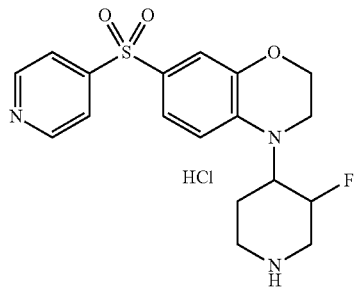

Step-1: 2-Nitro-5-(pyridin-4-sulfonyl)phenol

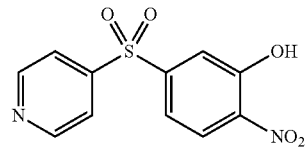

The title compound was synthesized from 2-nitro-5-(pyridin-4-ylsulfanyl)phenol following the procedure as described in step 1 of example 9.

Yield: 1.4 g (95%); $^1$H-NMR (DMSO-d$_6$, 400 MHz) δ ppm: 7.53-7.55 (d, J=8.04 Hz, 1H), 7.66-7.67 (m, 1H), 7.91-7.93 (m, 2H), 8.05-8.07 (d, J=8.16 Hz, 1H), 8.90-8.92 (m, 2H), 12.03 (bs, 1H); Mass (m/z): 279.2 (M−H)$^+$.

Racemic-4-(3-Fluoropiperidin-4-yl)-7-(pyridine-4-sulfonyl)-3,4-dihydro-2H-benzo[1,4]oxazine hydrochloride The title compound was synthesized by following the experimental procedures as described in intermediates 4 to 6, with some non-critical variations using 2-nitro-5-(pyridin-4-sulfonyl)phenol (obtained in above step) and appropriate intermediates. Mass (m/z): 378.4 (M+H)$^+$.

Example 11

7-Phenylsulfonyl-4-(3-fluoro-3-methylpiperidin-4-yl)-3,4-dihydro-2H-benzo[1,4]oxazine hydrochloride (First Eluting Isomer)

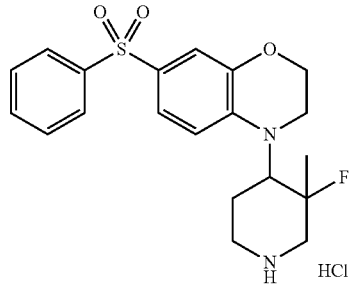

This example was prepared by following the experimental procedures as described in intermediate 6, with some non-critical variations using appropriate intermediates.

$^1$H-NMR (DMSO-d$_6$, 400 MHz) δ ppm: 1.46-1.52 (d, J=24.5 Hz, 3H), 2.02-2.05 (m, 2H), 3.07-3.08 (m, 1H), 3.29-3.31 (m, 2H), 3.39-3.47 (m, 3H), 4.12-4.18 (m, 2H), 4.39-4.45 (m, 1H), 7.07-7.09 (d, J=8.7 Hz, 1H), 7.13 (d, J=1.81 Hz, 1H), 7.30-7.33 (dd, J=1.5, 8.7 Hz, 1H), 7.54-7.63 (m, 3H), 7.85-7.87 (d, J=7.49 Hz, 2H), 8.97 (bs, 1H), 9.63 (bs, 1H); Mass (m/z): 391.3 (M+H)$^+$; HPLC (% purity): 99.79.

Example 12

7-Phenylsulfonyl-4-(3-fluoro-3-methylpiperidin-4-yl)-3,4-dihydro-2H-benzo[1,4]oxazine hydrochloride (Second Eluting Isomer)

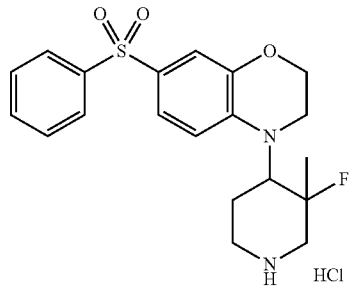

$^1$H-NMR (DMSO-d$_6$, 400 MHz) δ ppm: 1.26-1.32 (d, J=22.3 Hz, 3H), 1.76-1.79 (m, 1H), 2.17-2.26 (m, 1H), 3.05-3.10 (m, 1H), 3.32-3.49 (m, 5H), 4.08-4.20 (m, 2H), 4.29-4.39 (m, 1H), 7.12-7.15 (2H), 7.31-7.33 (dd, J=1.53, 8.67 Hz, 1H), 7.54-7.64 (m, 3H), 7.87-7.89 (d, J=7.44 Hz, 2H), 8.66 (bs, 1H), 9.53 (bs, 1H); Mass (m/z): 391.3 (M+H)$^+$; HPLC (% purity): 99.07.

Example 13

Racemic-6-Phenylsulfonyl-4-(3-fluoropiperidin-4-yl)-3,4-dihydro-2H-benzo[1,4]oxazine hydrochloride

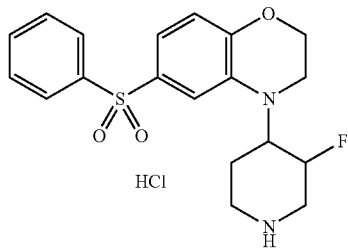

Step-1: 4-Phenylsulfonyl-2-nitro phenol

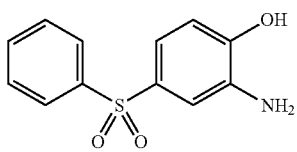

AlCl$_3$ (7.2 g, 0.53 mole) was added to 2-nitrophenol (5 g, 0.035 mole) at room temperature under mechanical stirring, maintained for ~15 min followed by the addition of benzenesulfonyl chloride (7.6 g, 0.043 mole). The reaction mixture was heated to 140° C. and maintained for 3 h to obtain a thick dark material. The reaction mixture was cooled to room temperature, added to cold water (250 mL), extracted with ethyl acetate (100 mL×3). The organic extracts were combined, dried over anhydrous Na$_2$SO$_4$, filtered and concentrated on rotavap to obtain crude mass which was purified by column chromatography using ethyl acetate: n-hexane (20:80) to obtain 4-phenylsulfonyl-2-nitro phenol.

Yield: 4.3 g (43%); $^1$H-NMR (DMSO-d$_6$, 400 MHz) δ ppm: 7.28-7.30 (d, J=8.9 Hz, 1H), 7.59-7.63 (m, 2H), 7.67-7.71 (m, 1H), 7.95-7.97 (d, J=8.81 Hz, 2H), 8.02-8.04 (dd, J=2.18, 8.95 Hz, 1H), 8.40-8.41 (d, J=2.14 Hz, 1H).

Step-2: 2-Amino-4-phenylsulfonyl phenol

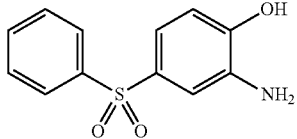

The title compound was synthesized from 4-phenylsulfonyl-2-nitro phenol following the procedure as described in Intermediate 3.

Yield: 3.4 g (89%); $^1$H-NMR (DMSO-d$_6$, 400 MHz) δ ppm: 5.03 (bs, 2H), 6.74-6.76 (d, J=8.2 Hz, 1H), 6.98-7.00 (dd, J=2.12, 8.16 Hz, 1H), 7.07-7.08 (d, J=2.08 Hz, 1H), 7.54-7.63 (m, 3H), 7.79-7.81 (d, J=7.2 Hz, 2H), 10.2 (bs, 1H); Mass (m/z): 248.4 (M−H)$^+$.

Step-3: tert-Butyl 4-(5-phenylsulfonyl-2-hydroxy phenylamino)-3-fluoro piperidin-1-carboxylate

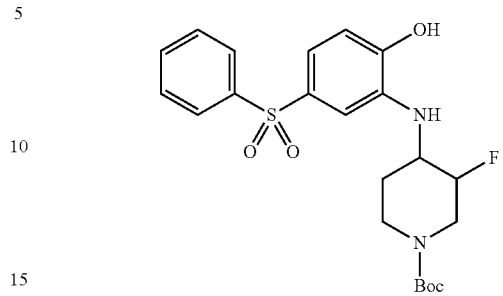

The title compound was synthesized from 2-amino-4-phenylsulfonyl phenol following the procedure as described in Intermediate 4. This compound was isolated as a diastereomeric mixture.

Yield: 2.4 g (85%); Mass (m/z): 449.1 (M−H)$^+$.

Step-4: tert-Butyl 4-[5-phenylsulfonyl-2-(2-chloroethoxy)phenylamino]-3-fluoro piperidin-1-carboxylate

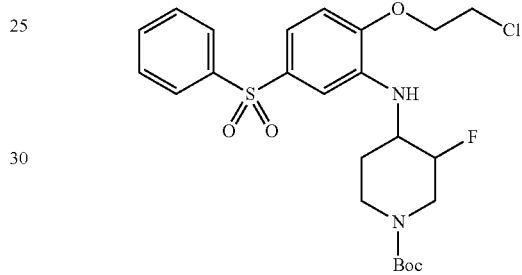

The title compound was synthesized from tert-butyl 4-(5-phenylsulfonyl-2-hydroxy-phenylamino)-3-fluoropiperidine-1-carboxylate following the procedure as described in Intermediate 5. This compound was isolated as a diastereomeric mixture.

Yield: 1.87 g (68%); HPLC (40.3%, 53.7%); Mass (m/z): 513.2 (M+H)$^+$.

Step-5: tert-Butyl 4-(6-phenylsulfonyl-3,4-dihydro benzo[1,4]oxazin-4-yl)-3-fluoro piperidin-1-carboxylate

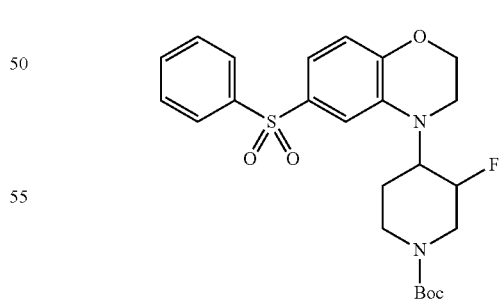

The title compound was synthesized from tert-butyl 4-[5-phenylsulfonyl-2-(2-chloroethoxy) phenylamino]-3-fluoro piperidin-1-carboxylate following the procedure as described in Intermediate 6. This compound was isolated as a diastereomeric mixture.

Yield: 0.39 g (23%); HPLC (40.3%, 53.7%); Mass (m/z): 477.2 (M+H)$^+$.

Step-6: Racemic-6-Phenylsulfonyl-4-(3-fluoropiperidin-4-yl)-3,4-dihydro-2H-benzo[1,4]oxazine hydrochloride

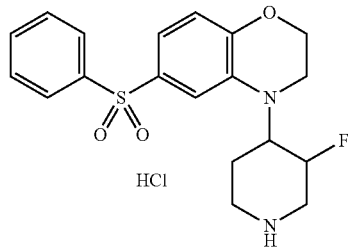

The title compound was synthesized from tert-butyl 4-(6-phenylsulfonyl-3,4-dihydro-benzo[1,4]oxazin-4-yl)-3-fluoropiperidin-1-carboxylate following the procedure as described in example 1. This compound was isolated as a diastereomeric mixture.

Yield: 0.62 g (87%); HPLC (47.08%, 47.30%); Mass (m/z): 377.2 (M+H)$^+$.

Example 14 to 17

The Examples 14 to 17 were obtained by chiral separation of 6-Phenylsulfonyl-4-(3-fluoro piperidin-4-yl)-3,4-dihydro-2H-benzo[1,4]oxazine hydrochloride (Example 13) in the form of free base using the method given below.

Method: Column ID: 250×4.6 mm, 5 μm, CHIRALPAK IC; Mobile Phase: 0.1% diethyl amine in methanol; Flow rate: 1 mL/min; Temp: 25° C.; Wavelength: 243 nM.

Example 14

6-Phenylsulfonyl-4-(3-fluoropiperidin-4-yl)-3,4-dihydro-2H-benzo[1,4]oxazine (Peak I)

Chiral HPLC 93.5%, (RT: 5.2 min), Mass (m/z): 377.1 (M+H)$^+$.

Example 15

6-Phenylsulfonyl-4-(3-fluoropiperidin-4-yl)-3,4-dihydro-2H-benzo[1,4]oxazine (Peak II)

Chiral HPLC 98.1%, (RT: 5.9 min), Mass (m/z): 377.5 (M+H)$^+$.

Example 16

6-Phenylsulfonyl-4-(3-fluoropiperidin-4-yl)-3,4-dihydro-2H-benzo[1,4]oxazine (Peak III)

Chiral HPLC 96.50%, (RT: 8.1 min), Mass (m/z): 377.1 (M+H)$^+$.

Example 17

6-Phenylsulfonyl-4-(3-fluoropiperidin-4-yl)-3,4-dihydro-2H-benzo[1,4]oxazine (Peak IV)

Chiral HPLC 98.1%, (RT: 15.1 min), Mass (m/z): 377.0 (M+H)$^+$.

Example 18

7-Phenylsulfonyl-4-[3-fluoro-1-(2-fluoroethyl)piperidin-4-yl]-3,4-dihydro-2H-benzo[1,4]oxazine (Peak III)

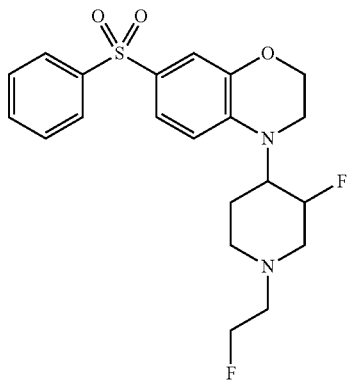

Cs$_2$CO$_3$ (0.097 g, 0.0003 mole) was added to a stirred solution of 7-phenylsulfonyl-4-(3-fluoropiperidin-4-yl)-3,4-dihydro-2H-benzo[1,4]oxazine hydrochloride (0.04 g, 0.00009 mole, Example 1) and 1-bromo-2-fluoroethane (0.037 g, 0.0003 mole) in acetonitrile (5 mL) and refluxed for 8 h. The reaction mixture was then cooled to room temperature, poured on to water (5 mL) and extracted with ethyl acetate (15 mL×3). The organic extracts were combined, dried over anhydrous Na$_2$SO$_4$, filtered and concentrated on rotavap to obtain crude mass which was purified by column chromatography using ethyl acetate:methanol (2:98) to the title compound.

Yield: 0.028 g (70%), $^1$H-NMR (DMSO-d$_6$, 400 MHz) δ ppm: 1.26-1.32 (d, J=22.3 Hz, 3H), 1.76-1.79 (m, 1H), 2.17-2.26 (m, 1H), 3.05-3.10 (m, 1H), 3.32-3.49 (m, 5H), 4.08-4.20 (m, 2H), 4.29-4.39 (m, 1H), 7.12-7.15 (2H), 7.31-7.33 (dd, J=1.53, 8.67 Hz, 1H), 7.54-7.64 (m, 3H), 7.87-7.89 (d, J=7.44 Hz, 2H), 8.66 (bs, 1H), 9.53 (bs, 1H); Mass (m/z): 423.1 (M+H)$^+$; HPLC (% purity): 99.07.

Example 19

7-Phenylsulfonyl-4-[3-fluoro-1-(2-fluoroethyl)piperidin-4-yl]-3,4-dihydro-2H-benzo[1,4]oxazine (Peak IV)

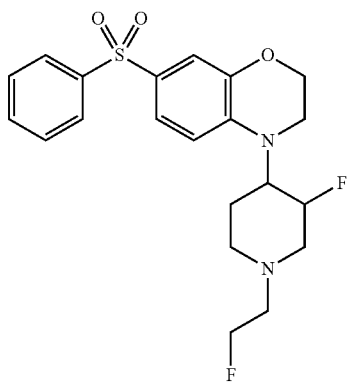

The title compound was synthesized from 7-phenylsulfonyl-4-(3-fluoropiperidin-4-yl)-3,4-dihydro-2H-benzo[1,4]oxazine hydrochloride (Example 4) following the procedure as described in Example 18.

Yield: 0.031 g (75%); $^1$H-NMR (CDCl$_3$, 400 MHz) δ ppm: 1.62-1.68 (m, 1H), 2.40-2.44 (m, 2H), 2.78-2.86 (m, 2H), 3.16-3.18 (m, 1H), 3.30-3.33 (m, 1H), 3.45-3.48 (m, 2H), 3.59-3.63 (m, 1H), 3.64-3.69 (m, 1H), 4.14-4.17 (m, 2H), 4.53-4.57 (m, 1H), 4.65-4.69 (m, 1H), 4.82-4.94 (d, J=49.35 Hz, 1H), 6.56-6.58 (d, J=8.72 Hz, 1H), 7.29-7.30 (m, 1H), 7.11-7.52 (m, 4H), 7.89-7.91 (d, J=7.27 Hz, 2H); Mass (m/z): 423.4 (M+H)$^+$; HPLC (% purity): 98.71.

Example 20

Determination of K$_b$ for 5-HT$_6$ Receptor:

A stable CHO cell line expressing recombinant human 5-HT$_6$ receptor and pCRE-Luc reporter system was used for cell based assay. The assay offers a non-radioactive based approach to determine binding of a compound to GPCRs. In this specific assay, the level of intracellular cyclic AMP which is modulated by activation or inhibition of the receptor is measured. The recombinant cells harbor luciferase reporter gene under the control of cAMP response element. The above cells were plated in 96 well clear bottom white plates at a density of 5×10$^4$ cells/well using Hams F12 medium containing 10% fetal bovine serum (FBS) and incubated overnight at 37° C. and 5% CO$_2$ followed by serum starvation for 18-20 hrs. Increasing concentrations of test compounds were added along with 10 μM serotonin in Opti-MEM to the cells. The incubation was continued at 37° C. in CO$_2$ incubator for 4 hours. After 4 hours cells were lysed using lysis buffer and luciferase assay buffer was added to each well and counts per second were recorded using luminescence counter. From counts per second (CPS) obtained, percent binding was calculated for each well by taking 10 μM 5-HT as 100% bound and vehicle as 0% bound. The percent bound values were plotted against compound concentrations and data were analyzed using a nonlinear, iterative curve-fitting computer program of Graph pad Prism 4 software. The K$_b$ values were calculated using concentration of the agonist used in the assay.

REFERENCES

Br. J. Pharmacol. 2006, 148, 1133-1143.
Mol. Brain Res. 2001, 90, 110-117.
Determination of 5-HT$_{2A}$ Binding:

Membrane preparation from recombinant human 5-HT$_{2A}$ cell line (Cat no. ES-313-M400UA) and radio ligand Ketanserin Hydrochloride, [Ethylene-$^3$H]-(R-41468) (Cat no. NET791250UC) were purchased from Perkin Elmer. All other reagents used in buffer preparation were purchased from Sigma. The final ligand concentration was 1.75 nM; non-specific determinant was 1-NP [10 μM] and 5-HT$_{2A}$ membrane protein (5 μg/well). 1-NP was used as a positive control. Reactions were carried out in 67 mM Tris pH 7.6 containing 0.5 mM EDTA buffer for 60 minutes at 25° C. Reaction was stopped by rapid filtration followed by six washes of the binding mixture using 96 well harvest plate (Millipore Cat no. MSFBNXB50) pre coated with 0.33% polyethyleneimine. The plate was dried and the bound radioactivity collected on the filters was determined by scintillation counting using MicroBeta TriLux. Radio ligand binding in the presence of non-labeled compound was expressed as a percent of the total binding and plotted against the log concentration of the compound. K$_i$ values were determined using a nonlinear, iterative curve-fitting computer program of Graph pad Prism 4 software.

REFERENCE

J. Pharmacol. Exp. Ther. 1993, 265, 1272-1279.

TABLE 1

| | In-vitro data | |
|---|---|---|
| Example No | 5-HT$_6$ K$_b$ (nM) | 5-HT$_{2A}$ K$_i$ (nM) |
| 1 | 0.04 | 130.4 |
| 2 | 0.4 | 261.6 |
| 3 | 0.09 | 112.6 |
| 4 | 0.4 | 3934 |
| 7 | <0.1 | 19.73 |
| 8 | 18.96 | 803.6 |
| 15 | 1.25 | 1660 |
| 17 | 1.79 | 907 |
| Comparator Example | 0.1 | 9.02 |

Conclusion

Above data clearly shows that the compounds of instant invention show high selectivity over 5-HT$_{2A}$ receptor as compared to the comparator example of U.S. Pat. No. 7,378,415.

Comparative Example

7-Phenylsulfonyl-4-(piperidin-4-yl)-3,4-dihydro-2H-benzo[1,4]oxazine

The comparative example is synthesized as per the U.S. Pat. No. 7,378,415 procedure.

Example 21

Rodent Pharmacokinetic Study

Male Wistar rats (260±50 grams) were used as experimental animals. Animals were housed individually in polypropylene cage. Two days prior to study, male Wistar rats were anesthetized with isoflurane for surgical placement of jugular vein catheter. Rats were randomly divided for oral (3 mg/kg) and intravenous (1 mg/kg) dosing (n=3/group) and fasted overnight before oral dosing (p.o.). However, rats allocated to intravenous dosing food and water was provided ad libitum.

At pre-determined point, blood was collected through jugular vein and replenished with an equivalent volume of normal saline. Collected blood was transferred into a labeled eppendorf tube containing 10 μL, of heparin as an anticoagulant. Typically blood samples were collected at following time points: 0.08, 0.25, 0.5, 1, 2, 4, 6, 8, and 24 hours post dose. Blood was centrifuged at 4000 rpm for 10 minutes. Plasma was separated and stored frozen at −80° C. until analysis. The concentrations of the test compounds were quantified in plasma by qualified LC-MS/MS method using suitable extraction technique. The test compounds were quantified in the calibration range around 1-1000 ng/mL in plasma. Study samples were analyzed using calibration samples in the batch and quality control samples spread across the batch.

Pharmacokinetic parameters C$_{max}$, AUC$_1$, T$_{1/2}$, Clearance and Bioavailability (F) were calculated by non-compartmental model using standard non-compartmental model by using Phoenix WinNonlin 6.2 or 6.4 version Software package.

TABLE 2

Pharmacokinetic profile

| Example No. | ROA | $C_{max}$ (ng/mL) | $AUC_{0-t}$ (ng · hr/mL) | $T_{1/2}$ (hr) | Clearance (mL/min/kg) | F (%) |
|---|---|---|---|---|---|---|
| 1 | oral (gavage) | 84 ± 14 | 1004 ± 15 | 5.6 ± 0.9 | — | 81 ± 1 |
|  | intravenous (bolus) | — | 412 ± 37 | 4.5 ± 0.1 | 40 ± 3 |  |

Example 22

Rodent Brain Penetration Study

Male Wistar rats (260±40 grams) were used as experimental animals. Three animals were housed in each cage. Animals were given water and food ad libitum throughout the experiment and maintained on a 12 hours light/dark cycle.

Brain penetration was determined in discrete manner in rats. One day prior to dosing day, male Wistar rats were acclimatized and randomly grouped according to their weight. At each time point (0.50, 1 and 2 hours) n=3 animals were used.

The test compounds were suitably preformulated and administered orally at (free base equivalent) 3 mg/kg. Blood samples were collected via cardiac puncture by using isoflurane anesthesia. The animals were sacrificed to collect brain tissue. Plasma was separated and brain samples were homogenized and stored frozen at −20° C. until analysis. The concentrations of the test compounds in plasma and brain were determined using LC-MS/MS method.

The test compounds were quantified in plasma and brain homogenate by qualified LC-MS/MS method using suitable extraction technique. The test compounds were quantified in the calibration range of 1-1000 ng/mL in plasma and brain homogenate. Study samples were analyzed using calibration samples in the batch and quality control samples spread across the batch. Extent of brain-plasma ratio (Cb/Cp) was calculated.

TABLE 3

Blood Brain Penetration data

| Example No. | Single dose rat brain penetration ($C_b/C_p$) at 3 mg/kg, p.o. |
|---|---|
| 1 | 0.78 ± 0.20 |

Example 23

Object Recognition Task Model

The cognition-enhancing properties of compounds of this invention were estimated using an animal model of cognition i.e., object recognition task.

Male Wistar rats (~230-280 grams) were used as experimental animals. Four animals were housed in each cage. Animals were kept on 20% food deprivation before one day and given water ad libitum throughout the experiment and maintained on a 12 hours light/dark cycle. The rats were habituated to individual arenas for 20 hour in the absence of any objects.

One group of 12 rats received vehicle (1 mL/kg) orally and another set of animals received compound of the formula (I) orally thirty minutes prior to familiar (T1) and choice trial (T2).

The experiment was carried out in a 50×50×50 cm open field made up of acrylic. During the familiarization phase (T1), the rats were placed individually in the open field for 3 minutes, in which two identical objects (plastic bottles, 12.5 cm height×5.5 cm diameter) covered in yellow masking tape alone (a1 and a2) were positioned in two adjacent corners (10 cm from the walls). After 24 hours of the (T1) trial, the same rats were placed in the same arena as they were placed in T1 trial. During the choice phase (T2) rats were allowed to explore the open field for 3 minutes in presence of one familiar object (a3) and one novel object (b) (Amber color glass bottle, 12 cm high and 5 cm in diameter). During the T1 and T2 trial, explorations of each object (defined as sniffing, licking, chewing or having moving vibrissae whilst directing the nose towards the object at a distance of less than 1 cm) were recorded separately by stopwatch.

T1 is the total time spent exploring the familiar objects (a1+a2).

T2 is the total time spent exploring the familiar object and novel object (a3+b).

REFERENCE

Behavioural Brain Research, 1988, 31, 47-59.

TABLE 4

Object Recognition Task data

| Example No | Dose mg/kg, p.o. | Exploration time mean ± S.E.M (sec) | | Inference |
|---|---|---|---|---|
| | | Familiar object | Novel object | |
| 1 | 0.1 | 7.03 ± 1.1 | 12.16 ± 0.72 | Active |

Example 24

Non-Clinical Toxicology

The safety of the example 1 of instant invention and comparator example of U.S. Pat. No. 7,378,415 were evaluated in repeated dose toxicity study in rat.

Female rats were used as experimental animals for evaluating the toxicity profile of example 1 of instant invention and the comparator example of U.S. Pat. No. 7,378,415.

During the study, female rats were dosed at incremental doses for minimum of 4 days. Toxicity assessment was done on the mortality, clinical observation, change in the body weight, feed consumption, clinical and anatomical pathology. Systemic exposures were also estimated for both of the compounds. All quantitative variables are compared with control group using one-way ANOVA followed by Dunnet's post-hoc test on GraphPad Prism Software version 4, 2003.

TABLE 5

Rat toxicity data

| S.no | Compound | Maximum Tolerated Dose | Findings | Repeated dose (4/7-Day) Toxicity (NOAEL, mg/kg) | $C_{max}$ | AUC |
|---|---|---|---|---|---|---|
| 1 | Example 1 | ≥300 mg/kg | No death up to the highest tested dose of 300 mg/kg | 4-Day repeat tox-NOAEL 300 mg/kg | 2420 ng/mL | 38100 ng*h/mL |
| 2 | Comparator example of U.S. Pat. No. 7,378,415 | 30 mg/kg | Mortality at ≥ 100 mg/kg on day 2 of dosing | 7-Day repeat tox-NOAEL 30 mg/kg | 280 ng/mL | 4050 ng*h/mL |

Results

In tested preclinical species, example 1 showed surprisingly superior safety profile as compared to the comparator example of U.S. Pat. No. 7,378,415. In study where example 1 was dosed, no deaths were observed at doses as high as 300 mg/kg and the plasma exposures reaching as high as 38100 ng*h/mL (AUC). On the contrary, in the study where the comparator example of U.S. Pat. No. 7,378,415 evaluated, deaths were observed at doses >100 mg/kg on second day of dosing and the plasma concentrations were noted was as low as 4050 ng*h/mL (AUC).

Example 25

Evaluation of Acetylcholine Modulation in Ventral Hippocampus of Male Wistar Rats Experimental Procedure Four groups of male Wistar rats (240-300 g body weight) were stereotaxically implanted with a microdialysis guide cannula in ventral hippocampus (AP: −5.2 mm, ML: +5.0 mm, DV: −3.8 mm) under isoflurane anesthesia. Co-ordinates were taken according to atlas for the rat brain (Paxinos and Watson 2004) with reference points taken from bregma and vertical from the skull. The rats were allowed to recover individually for four-five days in a round bottom Plexiglas bowl with free access to feed and water.

After surgical recovery of 4-5 days, male Wistar rats were connected to dual quartz lined two-channel liquid swivel (Instech, UK) on a counter balance lever arm, which allowed unrestricted movements of the animal. Sixteen hours before start of study, a pre-equilibrated microdialysis probe (4 mm dialysis membrane) was inserted into the ventral hippocampus through the guide cannula. On the day of study, probe was perfused with artificial cerebrospinal fluid (aCSF; NaCl 147 mM, KC13 mM, $MgCl_2$ 1 mM, $CaCl_2 \cdot 2H_2O$ 1.3 mM, $NaH_2PO_4 \cdot 2H_2O$ 0.2 mM and $Na_2HPO_4 \cdot 7H_2O$ 1 mM, pH 7.2) at a flow rate of 1.5 µL/min and a stabilization period of 2 h was maintained. Five basal samples were collected at 20 min intervals prior to the treatment of example 1 (10 mg/kg, p.o.) or vehicle.

For two groups of the male Wistar rats, donepezil (1 mg/kg, s.c.) was administered 30 min after administration of example 1 and for another group of rats donepezil (1 mg/kg, s.c.)+memantine (1 mg/kg, s.c.) combination administered 30 min after administration of example 1. Dialysate samples were collected for an additional period of 4 h post treatment of example 1. Dialysates were stored below −50° C. prior to analysis.

Quantitation of Acetylcholine

Acetylcholine in dialysate was quantified using LC-MS/MS method in the calibration range of 0.099 nmol/L-70.171 nmol/L.

Statistical Analysis

All microdialysis data for acetylcholine was plotted as percent change from mean dialysate basal concentrations with 100% defined as the average of five pre-dose values. The percent change in acetylcholine levels were compared with donepezil alone and donepezil or memantine combination using two-way analysis of variance (time and treatment), followed by Bonferroni's posttest. Area under the curve (AUC) values for percent change in acetylcholine levels were calculated and the statistical significance between the mean AUC value were compared against donepezil alone or donepezil and memantine combination treatment using one-way ANOVA followed by Dunnett's test. Statistical significance was considered at a p value less than 0.05. Incorrect probe placement was considered as criteria to reject the data from animal.

Reference: Paxinos G. and Watson C. (2004) Rat brain in stereotaxic coordinates. Academic Press, New York.

Results (I) Treatment with donepezil (1 mg/kg, s.c.) produced an increase in hippocampal acetylcholine levels and reached to the maximum of 888±85% of basal levels. Example 1 (10 mg/kg, p.o.) in combination with donepezil (1 mg/kg, s.c.) produced significant increase in acetylcholine levels and peak levels reached up to 1445±247% of pre-dose levels (FIG. 1a).

Mean area under the curve values (AUC) calculated after combination treatment of example 1 (10 mg/kg, p.o.) and donepezil were significantly higher compared to donepezil (1 mg/kg, s.c.) alone (FIG. 1b).

(II) Treatment with donepezil (1 mg/kg, s.c.) and memantine (1 mg/kg, s.c.) combination produced an increase in hippocampal acetylcholine levels to the maximum of 1170±270% of basal levels. Example 1 (10 mg/kg, p.o.) in combination with donepezil (1 mg/kg, s.c.) and memantine (1 mg/kg, s.c.) produced significant increase in acetylcholine levels and peak levels reached up to 2822±415% of pre-dose levels (FIG. 2(a)).

Figure 2:
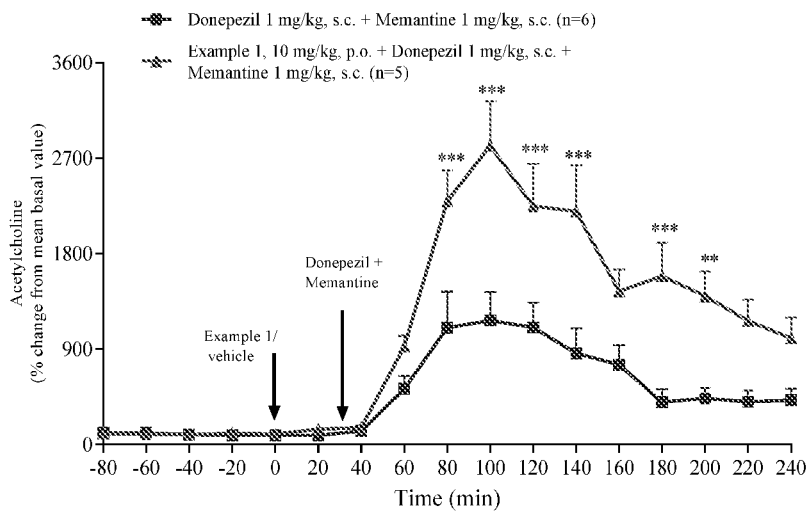
FIG. 2 depicts the effect of example 1, donepezil and memantine combination on extracellular levels of acetylcholine in ventral hippocampus of male Wistar rats.
Figure 2:
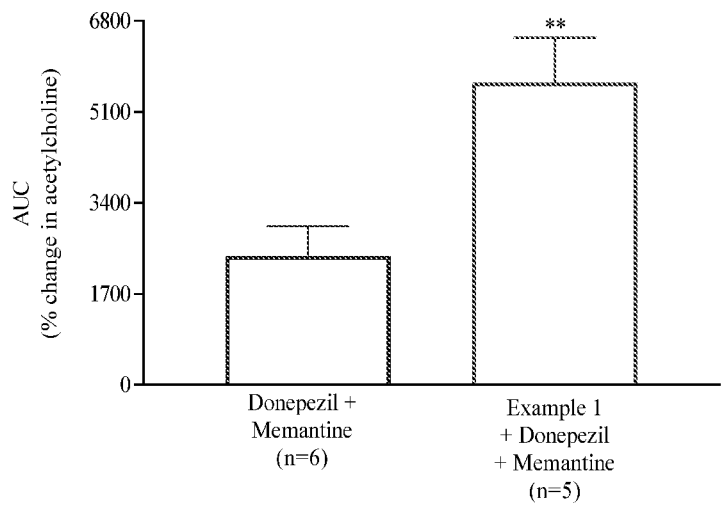

Mean area under the curve values (AUC) calculated after treatment of example 1 (10 mg/kg, p.o.), donepezil (1 mg/kg, s.c.) and memantine (1 mg/kg, s.c.) were significantly higher compared to donepezil (1 mg/kg, s.c.) and memantine (1 mg/kg, s.c.) combination (FIG. 2(b)).

We claim:
1. A fluoropiperidine compound of formula (I),

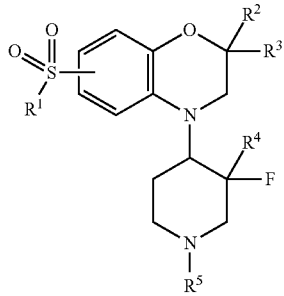

wherein:
R¹ represents phenyl or pyridyl; wherein the phenyl or pyridyl is optionally substituted with one or more groups selected from halogen, $(C_{1-6})$-alkyl or halo$(C_{1-6})$-alkyl;
R² represents hydrogen or $(C_{1-6})$-alkyl;
R³ represents hydrogen or $(C_{1-6})$-alkyl; or R² and R³ can combine together to form $(C_{3-6})$-cycloalkyl;
R⁴ represents hydrogen, $(C_{1-6})$-alkyl or halo$(C_{1-6})$-alkyl;
R⁵ represents hydrogen, $(C_{1-6})$-alkyl, halo$(C_{1-6})$-alkyl or —$(CH_2)_{0-3}$—$(C_{3-6})$-cycloalkyl;
or a stereoisomer or an isotopic form or a pharmaceutically acceptable salt thereof.

2. The compound as claimed in claim 1, wherein the compound is selected from the group consisting of:
7-Phenylsulfonyl-4-(3-fluoropiperidin-4-yl)-3,4-dihydro-2H-benzo[1,4]oxazine;
7-(3-Fluorophenylsulfonyl)-4-(3-fluoropiperidin-4-yl)-3,4-dihydro-2H-benzo[1,4]oxazine;
4-(3-Fluoropiperidin-4-yl)-7-(pyridine-2-sulfonyl)-3,4-dihydro-2H-benzo[1,4]oxazine;
4-(3-Fluoropiperidin-4-yl)-7-(pyridine-4-sulfonyl)-3,4-dihydro-2H-benzo[1,4]oxazine;
7-Phenylsulfonyl-4-(3-fluoro-3-methylpiperidin-4-yl)-3,4-dihydro-2H-benzo[1,4]oxazine;
6-Phenylsulfonyl-4-(3-fluoropiperidin-4-yl)-3,4-dihydro-2H-benzo[1,4]oxazine; and
7-Phenylsulfonyl-4-[3-fluoro-1-(2-fluoroethyl)piperidin-4-yl]-3,4-dihydro-2H-benzo[1,4]oxazine;
or a stereoisomer or an isotopic form or a pharmaceutically acceptable salt thereof.

3. The compound as claimed in claim 1, wherein the compound is selected from the group consisting of:
7-Phenylsulfonyl-4-(3-fluoropiperidin-4-yl)-3,4-dihydro-2H-benzo[1,4]oxazine hydrochloride (Peak III);
7-Phenylsulfonyl-4-(3-fluoropiperidin-4-yl)-3,4-dihydro-2H-benzo[1,4]oxazine hydrochloride (Peak I);
7-Phenylsulfonyl-4-(3-fluoropiperidin-4-yl)-3,4-dihydro-2H-benzo[1,4]oxazine hydrochloride (Peak II);
7-Phenylsulfonyl-4-(3-fluoropiperidin-4-yl)-3,4-dihydro-2H-benzo[1,4]oxazine hydrochloride (Peak IV);
7-(3-Fluorophenylsulfonyl)-4-(3-fluoropiperidin-4-yl)-3,4-dihydro-2H-benzo[1,4]oxazine hydrochloride (Peak I);
7-(3-Fluorophenylsulfonyl)-4-(3-fluoropiperidin-4-yl)-3,4-dihydro-2H-benzo[1,4]oxazine hydrochloride (Peak II);
7-(3-Fluorophenylsulfonyl)-4-(3-fluoropiperidin-4-yl)-3,4-dihydro-2H-benzo[1,4]oxazine hydrochloride (Peak III);
7-(3-Fluorophenylsulfonyl)-4-(3-fluoropiperidin-4-yl)-3,4-dihydro-2H-benzo[1,4]oxazine hydrochloride (Peak IV);
Racemic-4-(3-Fluoropiperidin-4-yl)-7-(pyridine-2-sulfonyl)-3,4-dihydro-2H-benzo[1,4]oxazine hydrochloride;
Racemic-4-(3-Fluoropiperidin-4-yl)-7-(pyridine-4-sulfonyl)-3,4-dihydro-2H-benzo[1,4]oxazine hydrochloride;
7-Phenylsulfonyl-4-(3-fluoro-3-methylpiperidin-4-yl)-3,4-dihydro-2H-benzo[1,4]oxazine hydrochloride (First eluting isomer);
7-Phenylsulfonyl-4-(3-fluoro-3-methylpiperidin-4-yl)-3,4-dihydro-2H-benzo[1,4]oxazine hydrochloride (Second eluting isomer);
Racemic-6-Phenylsulfonyl-4-(3-fluoropiperidin-4-yl)-3,4-dihydro-2H-benzo[1,4]oxazine hydrochloride;
6-Phenylsulfonyl-4-(3-fluoropiperidin-4-yl)-3,4-dihydro-2H-benzo[1,4]oxazine (Peak I);
6-Phenylsulfonyl-4-(3-fluoropiperidin-4-yl)-3,4-dihydro-2H-benzo[1,4]oxazine (Peak II);
6-Phenylsulfonyl-4-(3-fluoropiperidin-4-yl)-3,4-dihydro-2H-benzo[1,4]oxazine (Peak III);
6-Phenylsulfonyl-4-(3-fluoropiperidin-4-yl)-3,4-dihydro-2H-benzo[1,4]oxazine (Peak IV);
7-Phenylsulfonyl-4-[3-fluoro-1-(2-fluoroethyl)piperidin-4-yl]-3,4-dihydro-2H-benzo[1,4]oxazine (Peak III); and
7-Phenylsulfonyl-4-[3-fluoro-1-(2-fluoroethyl)piperidin-4-yl]-3,4-dihydro-2H-benzo[1,4]oxazine (Peak IV).

4. A pharmaceutical composition comprising the compound of formula (I) as claimed in claim 1 or a pharmaceutically acceptable salt thereof and pharmaceutically acceptable excipients, for the treatment of cognitive disorder, wherein said cognitive disorder is selected from the group consisting of dementia in Alzheimer's disease, dementia in Parkinson's disease, dementia in Huntington's disease, dementia associated with Down syndrome, frontotemporal dementia, Lewy body dementia, Vascular dementia, dementia in Creutzfeldt-Jakob disease, dementia in schizophrenia, and senile dementia.

5. A method of treatment of cognitive disorders comprising administering to a patient in need thereof, a therapeutically effective amount of the compound of formula (I) or a pharmaceutically acceptable salt thereof as claimed in claim 1, wherein the cognitive disorder is selected from the group consisting of dementia in Alzheimer's disease, dementia in Parkinson's disease, dementia in Huntington's disease, dementia associated with Down syndrome, frontotemporal dementia, Lewy body dementia, Vascular dementia, dementia in Creutzfeldt-Jakob disease, dementia in schizophrenia, and senile dementia.

6. A combination comprising the compound of formula (I) or a pharmaceutically acceptable salt thereof as claimed in claim 1 and an acetylcholinesterase inhibitor, for the treatment of cognitive disorders, wherein the acetylcholinesterase inhibitor is selected from galantamine, rivastigmine, donepezil, and tacrine or a pharmaceutically acceptable salt thereof.

7. A combination comprising the compound of formula (I) or a pharmaceutically acceptable salt thereof as claimed in claim 1, an acetylcholinesterase inhibitor and a NMDA receptor antagonist, for the treatment of cognitive disorders, wherein the acetylcholinesterase inhibitor is selected from galantamine, rivastigmine, donepezil, and tacrine or a pharmaceutically acceptable salt thereof and the NMDA receptor antagonist is selected from memantine or a pharmaceutically acceptable salt thereof.

8. The combination as claimed in claim 6, wherein the cognitive disorder is selected from group consisting of dementia in Alzheimer's disease, dementia in Parkinson's disease, dementia in Huntington's disease, dementia associated with Down syndrome, frontotemporal dementia, Lewy body dementia, Vascular dementia, dementia in Creutzfeldt-Jakob disease, dementia in schizophrenia, and senile dementia.

9. The combination as claimed in claim 7, wherein the cognitive disorder is selected from group consisting of dementia in Alzheimer's disease, dementia in Parkinson's disease, dementia in Huntington's disease, dementia associated with Down syndrome, frontotemporal dementia, Lewy body dementia, Vascular dementia, dementia in Creutzfeldt-Jakob disease, dementia in schizophrenia, and senile dementia.

10. A method of treating cognitive disorder comprising administering to the patient in need thereof, a therapeutically effective amount of compound of formula (I) or a pharmaceutically acceptable salt thereof as claimed in claim 2, wherein the cognitive disorder is selected from group consisting of dementia in Alzheimer's disease, dementia in Parkinson's disease, dementia in Huntington's disease, dementia associated with Down syndrome, frontotemporal dementia, Lewy body dementia, Vascular dementia, dementia in Creutzfeldt-Jakob disease, dementia in schizophrenia, and senile dementia.

11. A method of treating cognitive disorder comprising administering to the patient in need thereof, a therapeutically effective amount of compound of formula (I) or a pharmaceutically acceptable salt thereof as claimed in claim 3, wherein the cognitive disorder is selected from group consisting of dementia in Alzheimer's disease, dementia in Parkinson's disease, dementia in Huntington's disease, dementia associated with Down syndrome, frontotemporal dementia, Lewy body dementia, Vascular dementia, dementia in Creutzfeldt-Jakob disease, dementia in schizophrenia, and senile dementia.

* * * * *